United States Patent
Khuu-Duong et al.

(10) Patent No.: US 11,561,219 B2
(45) Date of Patent: Jan. 24, 2023

(54) METHODS OF ENUMERATING PARTICLES PRESENT IN A CELL COMPOSITION

(71) Applicant: Juno Therapeutics, Inc., Seattle, WA (US)

(72) Inventors: Kien Khuu-Duong, Snoqualmie, WA (US); Calvin Chan, Seattle, WA (US); Rachel K. Yost, Seattle, WA (US); Brian Christin, Seattle, WA (US); Ruth Berry, Bellevue, WA (US); Janelle Stoops, Marysville, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 559 days.

(21) Appl. No.: 16/326,553

(22) PCT Filed: Aug. 25, 2017

(86) PCT No.: PCT/US2017/048741
§ 371 (c)(1),
(2) Date: Feb. 19, 2019

(87) PCT Pub. No.: WO2018/039637
PCT Pub. Date: Mar. 1, 2018

(65) Prior Publication Data
US 2019/0187136 A1    Jun. 20, 2019

Related U.S. Application Data

(60) Provisional application No. 62/380,241, filed on Aug. 26, 2016.

(51) Int. Cl.
*G01N 33/543*    (2006.01)

(52) U.S. Cl.
CPC . *G01N 33/54333* (2013.01); *G01N 33/54313* (2013.01); *G01N 33/54326* (2013.01); *G01N 2446/20* (2013.01); *G01N 2446/86* (2013.01)

(58) Field of Classification Search
CPC ......... G01N 33/54333; G01N 2446/20; G01N 33/54313; G01N 33/54326
See application file for complete search history.

(56) References Cited

U.S. PATENT DOCUMENTS

| | | |
|---|---|---|
| 4,452,773 A | 6/1984 | Molday |
| 4,490,436 A | 12/1984 | Kawakami |
| 4,554,088 A | 11/1985 | Whitehead |

(Continued)

FOREIGN PATENT DOCUMENTS

| | | |
|---|---|---|
| CN | 101305087 | 11/2008 |
| CN | 101469310 | 7/2009 |

(Continued)

OTHER PUBLICATIONS

Miltenyi Biotec. Protocol for the removal of MACS GMP Expact Treg Beads (Jul. 2012)).*

(Continued)

*Primary Examiner* — Gailene Gabel
(74) *Attorney, Agent, or Firm* — Morrison & Foerster LLP

(57) ABSTRACT

Provided herein are methods of assessing or determining the presence or absence of particles, such as bead particles, present in a cell composition. Also provided are articles of manufacture and kits for use in the methods.

26 Claims, 6 Drawing Sheets

(56) References Cited

U.S. PATENT DOCUMENTS

| | | |
|---|---|---|
| 4,654,267 A | 3/1987 | Ugelstad |
| 4,774,265 A | 9/1988 | Ugelstad |
| 4,795,698 A | 1/1989 | Owen |
| 5,091,206 A | 2/1992 | Wang |
| 5,200,084 A | 4/1993 | Liberti |
| 5,232,782 A | 8/1993 | Charmot |
| 5,283,079 A | 2/1994 | Wang |
| 5,318,797 A | 6/1994 | Matijevic |
| 5,356,713 A | 10/1994 | Charmot |
| 5,395,688 A | 3/1995 | Wang |
| 5,583,054 A | 12/1996 | Ito et al. |
| 5,834,121 A | 11/1998 | Sucholeiki |
| 6,040,177 A | 3/2000 | Riddell |
| 6,074,884 A | 6/2000 | Siiman et al. |
| 6,342,396 B1 | 1/2002 | Perrin et al. |
| 8,012,750 B2 | 9/2011 | Har-Noy et al. |
| 8,398,741 B2 | 3/2013 | Kaneko |
| 2005/0277159 A1 | 12/2005 | Lehmann et al. |
| 2007/0026381 A1 | 2/2007 | Huang et al. |
| 2008/0317724 A1 | 12/2008 | Kam et al. |
| 2009/0156932 A1 | 6/2009 | Pavlovich et al. |
| 2010/0012880 A1 | 1/2010 | Rampersaud et al. |
| 2010/0207051 A1 | 8/2010 | Fonnum et al. |
| 2011/0003380 A1 | 1/2011 | Miltenyi |
| 2013/0330716 A1 | 12/2013 | Fabien et al. |
| 2014/0170678 A1 | 6/2014 | Kasdan et al. |
| 2020/0393355 A1 | 12/2020 | Livingston et al. |

FOREIGN PATENT DOCUMENTS

| | | |
|---|---|---|
| CN | 102516178 | 6/2012 |
| CN | 105200007 | 12/2015 |
| CN | 205279665 | 6/2016 |
| EP | 452342 | 10/1991 |
| EP | 1257632 | 11/2002 |
| EP | 1348943 | 10/2003 |
| JP | 2007254465 | 10/2007 |
| JP | 2007503377 | 7/2012 |
| JP | 2016-509846 | 4/2016 |
| WO | WO 1994/029436 | 12/1994 |
| WO | WO 1999/024045 | 5/1999 |
| WO | WO 1999/054439 | 10/1999 |
| WO | WO 2001/062895 | 8/2001 |
| WO | WO 2005/018667 | 8/2004 |
| WO | WO 2005/051990 | 6/2005 |
| WO | WO 2005/113003 | 12/2005 |
| WO | WO 2006/037649 | 4/2006 |
| WO | WO 2008/041004 | 4/2008 |
| WO | WO 2008/052338 | 5/2008 |
| WO | WO 2009/072003 | 6/2009 |
| WO | WO 2010/057318 | 5/2010 |
| WO | WO 2010/099205 | 9/2010 |
| WO | WO 2010/140127 | 12/2010 |
| WO | WO 2011/109440 | 9/2011 |
| WO | WO 2012/064878 | 5/2012 |
| WO | WO 2014/138887 | 9/2014 |
| WO | WO 2014/151763 | 9/2014 |
| WO | WO 2016/090190 | 6/2016 |

OTHER PUBLICATIONS

Laberriere et al. Full GMP Process to Select and Amplify Epitope-Specific T Lymphocytes for Adoptive Immunotherapy of Metastatic Melanoma. Clinical and Developmental Immunology. vol. 2013. Article 932318 (Aug. 2013).*

Hollyman et al., "Manufacturing validation of biologically functional T cells targeted to CD19 antigen for autologous adoptive cell therapy," J Immunother. (2009) 32(2):169-180.

Labarriere et al., "A full GMP process to select and amplify epitope-specific T lymphocytes for adoptive immunotherapy of metastatic melanoma," Clin Dev Immunol. (2013) 2013:932318 (11 pgs).

Van der Stegen, An investigation into the potential toxicity of erbb targeting t4 immunotherapy, Submitted to King's College London for the award of Doctor of Philosophy, Jul. 2013, pp. 220-235 Chapter 5, URL, https://kclpure.kcl.ac.uk/portal/files/32139513/2013_van_der_Stegen_Sjoukje_ethesis.pdf.

Anonymous, "DynaMag™ CTS™ Magnet Manual," Life Technologies, Apr. 17, 2013.

Anonymous, "Protocol for the removal of Macs® GMP ExpAct Treg Beads," Miltenyi Biotec, available at https://www.miltenyibiotec.com/upload/assets/IM0017462.PDF, Jul. 2012, retrieved Apr. 11, 2019.

Crapo et al., "An overview of tissue and whole organ decellularization processes." Biomaterials. Apr. 2011;32(12):3233-43.

Entschladen et al., "Differential requirement of protein tyrosine kinases and protein kinase C in the regulation of T cell locomotion in three-dimensional collagen matrices," J Immunol. (1997) 159(7):3203-3210.

Friedl et al.," T lymphocyte locomotion in a three-dimensional collagen matrix Expression and function of cell adhesion molecules," J Immunol. (1995) 154:4973-4985.

Giouroudi et al., "Microfluidic Biosensing Systems Using Magnetic Nanoparticles," Int J Mol Sci., (2013) 14(9): 18535-18556.

Kinosita et al., "Hemolysis of human erythrocytes by a transient electric field," Proc. Natl. Acad. Sci., (1977) 74:1923-7.

Klebanoff et al., "Sorting through subsets: Which T cell populations mediate highly effective adoptive immunotherapy?," J Immunother. (2012) 35(9): 651-660.

Li et al., "Comparison of anti-CD3 and anti-CD28-coated beads with soluble anti-CD3 for expanding human T cells: Differing impact on CD8 T cell phenotype and responsiveness to restimulation," J Transl Med., (2010) 8:104.

Mescher, "Surface contact requirements for activation of cytotoxic T lymphocytes," J. Immunol., (1992) 149(7):2402-2405.

Prufer et al., "Oxidative burst and neutrophil elastase contribute to clearance of Aspergillus fumigatus pneumonia in mice." Immunobiology. Feb. 2014;219(2):87-96.

Steenbloc et al., "A comprehensive platform for ex vivo T-cell expansion based on biodegradable polymeric artificial antigen-presenting cells," Molecular Therapy, (2008) 16(4)765-772.

Terakura et al., "Generation of CD19-chimeric antigen receptor modified CD8+T cells derived from virus-specific central memory T cells," Blood. (2012) 119(1)72-82.

Wang et al., "Phenotypic and Functional Attributes of Lentivirus Modified CD19-specific Human CD8+ Central Memory T Cells Manufactured at Clinical Scale," J Immunother. (2012) 35(9):689-701.

He et al., Medical Research Methodology, People's Military Medical Press, p. 90, published on Oct. 31, 2003 (English translation provided).

Li et al., "Expression of plasma vascular endothelial growth factor in patients with hepatocellular carcinoma and effect of transcatheter arterial chemoembolization therapy on plasma vascular endothelial growth factor level," World J Gastroenterol. (2004) 10(19) 2878-82.

Phanse et al., "Analyzing cellular internalization of nanoparticles and bacteria by multi-spectral imaging flow cytometry," J Vis Exp. (2012) (64): e3884.

Won et al., "Flow cytometric detection of erythrocyte osmotic fragility," Cytometry B Clin Cytom. (2009) 76(2): 135-41.

Aarvak et al., "Dynabeads CD3/CD28 CTS™ for T cell isolation, activation and expansion." Poster, (2007).

Clarke and Davies in: Methods in Molecular Medicine, vol. 58: Metastasis Research Protocols, vol. 2: Cell Behavior In Vitro and In Vivo, Edited by: S. A. Brooks and U. Schumacher© Humana Press Inc., Totowa, NJ (2001) pp. 17-25.

Evans et al., "High-permeability functionalized silicone magnetic microspheres with low autofluorescence for biomedical applications." Mater Sci Eng C Mater Biol Appl. (2016) 62: 860-869.

Klamp et al., "Highly Rapid Amplification-Free and Quantitative DNA Imaging Assay." Scientific Reports. (2013) 3(1852): 1-7.

Koga et al., "Usefulness of Immuno-Magnetic Beads conjugated with Anti-EpCAM Antibody for Detecting Endometrial Cancer Cells." Journal of Cancer Therapy. 2013. 4:1273-1282.

(56) References Cited

OTHER PUBLICATIONS

Li et al., "Clinical significance of osmolality measurement." Shaanxi Medical Journal (1989) 18 (8): 40-43.
Li et al. "Effect of transcatheter arterial chemoembolization on the circulating tumor cells number and the vascular endothelial growth factor concentration in patients with hepatocellular carcingma," Chinese Clinical Oncology (2015) 20 (8): 709-712, Abstract only) (Abstract translation).
Molecular Probes CAL-LYSE Lysing Solution User guide (Catalog numbers GAS-010, GAS-010S-100), (2013).
Molecular Probes CountBrighthsplute Counting Beads *for flow cytometry* Product Information (MP 36950), (2005).
Young et al., "Assessment of enhanced autofluorescence and impact on cell microscopy for microfabricated thermoplastic devices." Anal Chem. (2013) 85(1): 44-49.
Klamp et al., "Highly Rapid Amplification-Free and Quantitative DNA Imaging Assay." Supplementary Information. Scientific Reports. 2013. 3(1852): 1-7.

* cited by examiner

METHODS OF ENUMERATING PARTICLES PRESENT IN A CELL COMPOSITION

CROSS-REFERENCE TO RELATED APPLICATIONS

This application is a U.S. National Stage under 35 U.S.C. § 371 of International Application No. PCT/US2017/048741, filed Aug. 25, 2017, which claims the benefit of priority to U.S. provisional patent application No. 62/380,241, filed Aug. 26, 2016, entitled "METHODS OF ENUMERATING PARTICLES PRESENT IN A CELL COMPOSITION" the contents of which are hereby incorporated by reference in their entirety for all purposes.

FIELD

The present disclosure relates to methods of assessing or determining the presence or absence of particles, such as bead particles, present in a cell composition. Also provided are articles of manufacture and kits for use in the methods.

BACKGROUND

Particles, such as magnetic beads, are used as a surface for immobilization of affinity reagents, such as antibodies. In some cases, such affinity coated particles can be used in various methods, such as in detection, selection, enrichment, isolation, activation and/or stimulation of cells. In some cases, affinity coated particles can remain bound to cells after such processes. Current methods for detecting the presence or absence of particles in a cell composition can be inaccurate for determining the actual number of particles bound or associated with a cell. Improved methods for enumerating or detecting particles in a cell composition are needed. Provided herein are methods, compositions, systems, and kits that meet such needs.

SUMMARY

Provided are methods for assessing or determining the presence or absence of particles in a cell composition, such as bead particles comprising an antibody (e.g., an anti-CD3 antibody and/or an anti-CD28 antibody). Such methods include methods for detecting the presence or absence of particles in a cell composition and methods for enumerating particles in a cell composition. The present disclosure also provides articles of manufacture and kits for use in the methods.

Provided herein, in some embodiments, are methods for enumerating or detecting the presence or absence of particles in a cell composition, the method comprising the steps of a) performing one or more incubations, thereby producing an output composition, wherein the one or more incubations in step a) comprises i) incubating a sample comprising at least a portion of a cell composition or a sample derived from the cell composition under a condition sufficient to induce osmotic lysis of one or more cells in the sample, and b) determining the presence, absence, number and/or concentration of particles in the output composition, thereby enumerating or detecting the presence or absence of particles in the cell composition. In some embodiments, the condition sufficient to induce osmotic lysis comprises contacting the sample with a hypotonic solution. In some embodiments, the incubating under a condition to induce osmotic lysis produces a lysed cell composition and the one or more incubations in step a) further comprises ii) incubating the lysed cell composition or a composition derived from the lysed cell composition with a hypertonic solution. In some embodiments, the one or more incubations in step a) reduces or removes cell debris from the output composition. In some embodiments of the methods herein, step a) further comprises rinsing or washing the output composition. In some further embodiments, rinsing or washing the output composition comprises pelleting the particles and removing a volume or reducing a volume of the output composition. In some embodiments, the method further comprises reducing the volume of the output composition to about the same volume of the sample prior to the one or more incubations of step a). In some embodiments, the method further comprising reducing the volume of the output composition by less than 100% but greater than or greater than about 50%, 60%, 70%, 80%, 90% or 95%.

In some embodiments, provided herein, are methods for enumerating or detecting the presence or absence of particles in a cell composition, the method comprising the steps of a) performing one or more incubations, thereby producing an output composition, wherein the one or more incubations in step a) comprises i) incubating a sample comprising at least a portion of a cell composition or a sample derived from the cell composition with a hypotonic solution or a hypertonic solution under a condition sufficient to induce lysis of one or more cells in the sample, thereby producing a lysed cell composition, and ii) incubating at least a portion of the lysed cell composition or a sample derived from the lysed cell composition with the other of the hypotonic solution or the hypertonic solution; and, and b) determining the presence, absence, number and/or concentration of particles in the output composition, thereby enumerating or detecting the presence or absence of particles in the cell composition In some embodiments, the one or more incubations in step a) reduces or removes cell debris from the output composition. In some embodiments of the methods herein, step a) further comprises rinsing or washing the output composition. In some further embodiments, rinsing or washing the output composition comprises pelleting the particles and removing a volume or reducing a volume of the output composition. In some embodiments, the method further comprises reducing the volume of the output composition to about the same volume of the sample prior to the one or more incubations of step a). In some embodiments, the method further comprising reducing the volume of the output composition by less than 100% but greater than or greater than about 50%, 60%, 70%, 80%, 90% or 95%.

Provided herein, in some embodiments, are methods for enumerating or detecting the presence or absence of particles in a cell composition, the method comprising the steps of a) performing one or more incubations, thereby producing an output composition, wherein the one or more incubations in step a) comprises i) incubating a sample comprising at least a portion of a cell composition or a sample derived from the cell composition with a hypotonic solution under a condition sufficient to induce lysis of one or more cells in the sample, thereby producing a lysed cell composition, and ii) incubating at least a portion of the lysed cell composition or a sample derived from the lysed cell composition with a hypertonic solution, and b) determining the presence, absence, number and/or concentration of particles in the output composition, thereby enumerating or detecting the presence or absence of particles in the cell composition. In some embodiments, the one or more incubations in step a) reduces or removes cell debris from the output composition. In some embodiments of the methods herein, step a) further comprises rinsing or washing the output composition. In some further embodiments, rinsing or washing the output composition comprises pelleting the particles and removing a volume or reducing a volume of the output composition. In some embodiments, the method further comprises reducing the volume of the output composition to about the same volume of the sample prior to the one or more incubations of step a). In some embodiments, the method further comprising reducing the volume of the output composition by less than 100% but greater than or greater than about 50%, 60%, 70%, 80%, 90% or 95%.

Also provided herein, in some embodiments, are methods of enumerating or detecting the presence or absence of particles in a cell composition, the method comprising the steps of a) performing one or more incubations, thereby producing an output composition, wherein the one or more incubations in step a) comprises i) incubating a sample comprising at least a portion of a cell composition or a sample derived from the cell composition, under a condition sufficient to induce lysis of one or more cells in the sample, wherein the particle comprises a coat comprising a biomolecule (e.g. a polysaccharide) on its surface and the lysis does not destroy the coat; and b) determining the presence, absence, number and/or concentration of particles in the output composition using an affinity reagent that specifically binds to the biomolecule (e.g., polysaccharide), thereby enumerating or detecting the presence or absence of particles in the cell composition. In some embodiments, the one or more incubations induces osmotic cell lysis of one or more cells in the sample. In some embodiments, the one or more incubations comprises incubating the sample with a hypotonic solution. In some embodiments, the one or more incubations further comprises incubating the sample with a hypertonic solution. In some embodiments, the biomolecule is dextran and the affinity reagent is an anti-dextran antibody. In some embodiments, the biomolecule is a first antibody (e.g., mouse antibody) and the affinity reagent is a second antibody (e.g., anti-mouse antibody). In some embodiments, the biomolecule is streptavidin and the affinity reagent is a biotinylated molecule. In some embodiments, the biomolecule is streptavidin and the affinity reagent is an anti-streptavidin antibody. In some embodiments, the determining in step b) comprises fluorescence-activated cell sorting (FACS) for detection of one or more of the particles comprising the coat.

In some embodiments provided herein, the hypotonic solution has an osmolarity less than 270 mOsm/L. In some embodiments, the hypotonic solution has an osmolarity between or between about 0 mOsm/L and 270 mOsm/L, 50 mOsm/L and 200 mOsm/L or 10 mOsm/L and 100 mOsm/L. In some embodiments, the hypotonic solution has an osmolarity less than or less than about 250 mOsm/L, 200 mOsm/L, 150 mOsm/L, 100 mOsm/L, 50 mOsm/L, 10 mOsm/L or less. In some embodiments, the hypotonic solution comprises a solute concentration of between or between about 0 mM and 140 mM. In some embodiments, the hypotonic solution comprises a solute concentration of less than or about less than 140 mM, less than or about less than 100 mM, less than or about less than 50 mM or less than or about less than 10 mM. In some embodiments, the hypotonic solution comprises a percentage weight for volume (% w/v) of solute of between or between about 0% and 0.8% or 0% and 0.5%. In some embodiments, the hypotonic solution comprises a % w/v of solute of less than or about less than 0.8%, less than or about less than 0.6%, less than or about less than 0.4% or less than or about less than 0.2%. In some embodiments, the hypotonic solution is solute-free. In some embodiments, the hypotonic solution is sterile water for injection.

In some embodiments provided herein, the hypertonic solution has an osmolarity greater than 300 mOsm/L. In some embodiments, the hypertonic solution has an osmolarity of greater than or about 300 mOsm/L, greater than or about 400 mOsm/L, greater than or about 800 mOsm/L, greater than or about 1200 mOsm/L, greater than or about 1500 mOsm/L, greater than or about 2000 mOsm/L, greater than or about 2500 mOsm/L, greater than or about 3000 mOsm/L or greater than or about 4000 mOsm/L. In some embodiments, the hypertonic solution has an osmolarity of between or about between 300 mOsm/L and 5000 mOsm/L, 1000 and 5000 mOsm/L or 1000 and 3000 mOsm/L. In some embodiments, the hypertonic solution has a solute concentration of greater than or about 200 mM, greater than or greater than about 400 mM, greater than or greater than about 600 mM, greater than or greater than about 800 mM, greater than or greater than about 1000 mM greater than or greater than about 2000 mM; or greater than or greater than about 5000 mM. In some embodiments, the hypertonic solution has a solute concentration of between or between about 200 mM and 5000 mM, 500 mM and 2000 mM or 1000 mM and 2000 mM. In some embodiments, the hypertonic solution comprises a percentage weight for volume (% w/v) of solute of between or between about 1.5% and 15% or 2.5% and 12%. In some embodiments, the hypertonic solution comprises a % w/v of solute of greater than or about greater than 1.5%, greater than or about greater than 3.0%, greater than or about greater than 6.0% or greater than or about greater than 8.0% or greater than or about greater than 10.0%. In some embodiments, the hypertonic solution comprises a solute that is NaCl.

In some of any such embodiments, the volume of the hypotonic and/or hypertonic solution is at least or at least about 1 mL, 3 mL, 9 mL, 12 mL, 15 mL, 18 mL, 20 mL, 25 mL, 30 mL, 35 mL, 40 mL, 45 mL, 50 mL or more. In some of any such embodiments, the volume of the hypotonic and/or hypertonic solution is from or from about 1 mL to 50 mL, 2 mL to 30 mL, 5 mL to 25 mL or 10 mL to 20 mL.

In some of any such embodiments, the one or more incubation is for at least or at least about 30 seconds, 1 minute, 2 minutes, 3 minutes, 4 minutes, 5 minutes, 10 minutes, 20 minutes or 30 minutes. In some of any such embodiments, the one or more incubation is from or from about 30 seconds to 30 minutes, 1 minute to 20 minutes, 1 minute to 10 minutes or 1 minute to 5 minutes.

In some of any such embodiments, the one or more incubations in step a) is/are performed at a temperature that is about 15° C. to 30° C., 18° C. to 28° C. or 20° C. to 25° C. In some of any such embodiments, the one or more incubations in step a) is/are performed at a temperature that is or is about 23° C. In some of any such embodiments, the one or more incubations in step a) is/are performed at a temperature that is or is about 24° C. In some of any such embodiments, the one or more incubations in step a) is/are performed at a temperature that is or is about 25° C.

In some of any such embodiments, the determining in step b) comprises manual counting, electronic particle counting, affinity-based detection, microscopy (e.g., fluorescent microscopy), flow cytometry, or magnetic cell sorting.

In some of any such embodiments, the determining in step b) comprises fluorescence-activated cell sorting (FACS) for detection of one or more of the particles comprising a coat, wherein the coat comprises a material described herein such as a polymer. In some embodiments, the material is a polysaccharide. In some embodiment, the polysaccharide is dextran and the affinity reagent is an anti-dextran antibody. In some embodiments, the material is a first antibody (e.g., mouse antibody) and the affinity reagent is a second antibody (e.g., anti-mouse antibody). In some embodiments, the material is streptavidin and the affinity reagent is a biotinylated molecule. In some embodiments, the material is streptavidin and the affinity reagent is an anti-streptavidin antibody.

In some of any such embodiments, the cell composition comprises or is suspected of comprising one or more of the particles bound to the surface of one or more cells in the cell composition, the cell composition comprises or is suspected of comprising residual particles, the cell composition is derived from a composition containing cells bound to one or more of the particles, and/or the cell composition is derived from removal of particles from an input composition.

In some of any such embodiments, the cell composition is produced by a method comprising i) mixing a population of cells with one or more of the particles thereby generating an input composition; and ii) removing one or more of the particles from the cells in the input composition, thereby producing the cell composition. In some embodiments, the one or more of the particles are capable of binding one or more cells in the population.

In some of any such embodiments, the concentration of the cell composition is at least or at least about $2\times10^5$ cells/mL, at least or at least about $5\times10^5$ cells/mL, at least or at least about $1\times10^6$ cells/mL, at least or at least about $5\times10^6$ cells/mL, or at least or at least about $1\times10^7$ cells/mL.

In some of any such embodiments, the volume of the cell composition is from or from about 0.2 mL to 50 mL, 0.2 mL to 20 mL, 0.5 mL to 10 mL, 0.5 mL to 5 mL, or 0.75 mL to 1.5 mL. In some of any such embodiments, the volume of the cell composition is at least or at least about 0.2 mL, 0.5 mL, 1.0 mL, 2.0 mL, 5.0 mL, 10.0 mL or 20 mL, 50 mL or more.

In some of any such embodiments, the cell has a diameter of between or about between 10 μm and 30 μm.

In some of any such embodiments, the cell is an animal cell or the cell composition comprises animal cells. In some of any such embodiments, the cell is a human cell or the cell composition comprises human cells. In some of any such embodiments, the cell is a stem cell or the cell composition comprises stem cells. In a further embodiment, the stem cell is an induced pluripotent stem cell (iPSC). In some of any such embodiments, the cell is an immune cell or the cell composition comprises immune cells. In a further embodiment, the immune cell is a T cell, B cell, macrophage, neutrophil, natural killer (NK) cell or dendritic cell.

In some of any such embodiments, the cell composition has been mixed with one or more of the particles, wherein the particle comprises a stimulating agent to effect stimulation and/or activation of a cell in the cell composition prior to the one or more incubations in step a). In a further embodiment, the cell is a T cell and the stimulating agent is an anti-CD3 antibody and/or anti-CD28 antibody or an antigen-binding fragment thereof. In another further embodiment, the cell is an antigen presenting cell and the stimulating agent is an anti-CD80 antibody and/or anti-CD86 antibody or an antigen-binding fragment thereof.

In some of any such embodiments, the cell composition has been mixed with one or more of the particles, wherein the particle comprises an affinity agent to effect isolation or enrichment of a cell in the cell composition prior to the one or more incubations in step a). In a further embodiment, the affinity reagent comprises an antibody or antigen-binding fragment thereof that specifically binds to a cell surface protein on one or more cells in the cell composition. In a further embodiment, the cell surface protein is selected from among, but are not limited to, CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD1 1a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3.

In some of any such embodiments, one or more of the particles comprises a biomolecule (e.g., an affinity reagent or stimulating agent) capable of binding to a macromolecule on a surface of a cell (e.g., a cell surface protein) in the cell composition. In some embodiments, the biomolecule is an antibody or an antigen-binding fragment thereof. In some embodiments, the biomolecule is streptavidin. In some of any such embodiments, the particles are bead particles. In particular embodiments, the particles are bead particles comprising an antibody (e.g., anti-CD3 antibody and/or anti-CD28 antibody) and/or a coat such as a coat as described herein.

In some of any such embodiments, one or more of the particles have or comprise particles having a diameter of greater than 0.001 μm, greater than 0.01 μm, greater than 0.1 μm, greater than 1.0 μm, greater than 10 μm, greater than 50 μm, greater than 100 μm or greater than 1000 μm. In some of any such embodiments, one or more of the particles have or comprise particles having a diameter of 1.0 μm to 500 μm, 1.0 μm to 150 μm, 1.0 μm to 30 μm, 1.0 μm to 10 μm or 1.0 μm to 5.0 μm. In some embodiments, one or more of the particles have or comprise particles having a diameter that is substantially the same as the average diameter of a cell in the cell composition. In some embodiments, one or more of the particles have or comprise particles having a diameter that is within 1.5-fold greater or less than the average diameter of a cell in the cell composition.

In some of any such embodiments, one or more of the particles comprises a coat. In some embodiments, the coat comprises a polymer, a polysaccharide, a silica, a fatty acid, a carbon or a combination thereof. In some embodiments, the polymer, the polysaccharide, the silica, the fatty acid, the carbon or a combination thereof is biodegradable. In some embodiments, the polysaccharide is chitosan, agarose, starch, dextran, a dextran derivative or combinations thereof. In some embodiments, the polymer is polyethylene glycol, poly(lactic-co-glycolic acid), polyglutaraldehyde, polyurethane, polystyrene, and polyvinyl alcohol or combinations thereof. In some embodiments, the coat is on the surface of the particle.

In some of any such embodiments, one or more of the particles is magnetic. In some of any such embodiments, one or more of the particles comprise a magnetic core, a paramagnetic core or a superparamagnetic core. In some further embodiments, the magnetic core is selected from among metal oxides, ferrites, metals, hematite, metal alloys, and combinations thereof. In some of any such embodiments, one or more of the particles comprise an iron oxide core. In some embodiments, the magnetic core comprises a coat such as a coat described herein (e.g., a coat comprising polymer, a polysaccharide, a silica, a fatty acid, a carbon or a combination thereof). In some embodiments, the coat protects, reduces or prevents the magnetic core from oxidation. In some embodiments, the coat is on the surface of the particle.

In some of any such of the embodiments, the methods provided herein do not destroy the coat on the surface of the particle.

Also provided is an article of manufacture that includes a container comprising a solution for effecting osmotic cell lysis, a hypotonic solution and/or a hypertonic solution; packaging material; and a label or package insert comprising instructions for enumerating or detecting the presence or absence of particles in a cell composition. In some embodiments, the solution that effects osmotic lysis is a hypotonic solution, and the article of manufacture optionally further comprises a container comprising a hypertonic solution. In some embodiments, the article of manufacture further comprises an instrument or reagent for detecting or identifying particles. In some embodiments, the instrument or reagent comprises a hemocytometer. In some embodiments, the instrument or reagent comprises an affinity reagent specific for a biomolecule on the surface of the particle, such as a polysaccharide (e.g., dextran), an antibody, or any other biomolecule (e.g., streptavidin) that can be bound by the affinity reagent. In some embodiments, the affinity reagent is or comprises an antibody or antigen-binding fragment, such as an anti-dextran antibody or antigen-binding fragment. In some embodiments, the affinity reagent is fluorescently labeled.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A) The number of bead particles in a sample not treated with bleach as determined by scatter; FIG. 1B) the number of bead particles in a sample not treated with bleach as determined by staining with a fluorescently labeled anti-dextran antibody; FIG. 1C) the number of bead particles in a sample not treated with bleach as determined by staining with fluorescently labeled anti-IgG1 and anti-IgG2a antibodies; FIG. 1D) The number of bead particles in a sample treated with bleach as determined by scatter; FIG. 1E) the number of bead particles in a sample treated with bleach as determined by staining with a fluorescently labeled anti-dextran antibody; FIG. 1F) the number of bead particles in a sample treated with bleach as determined by staining with fluorescently labeled anti-IgG1 and anti-IgG2a antibodies. Arrows indicate bead particles. "SSC-A" and "FSC-A" indicate side scatter and forward scatter parameters, respectively.

DETAILED DESCRIPTION

Figure 1B:
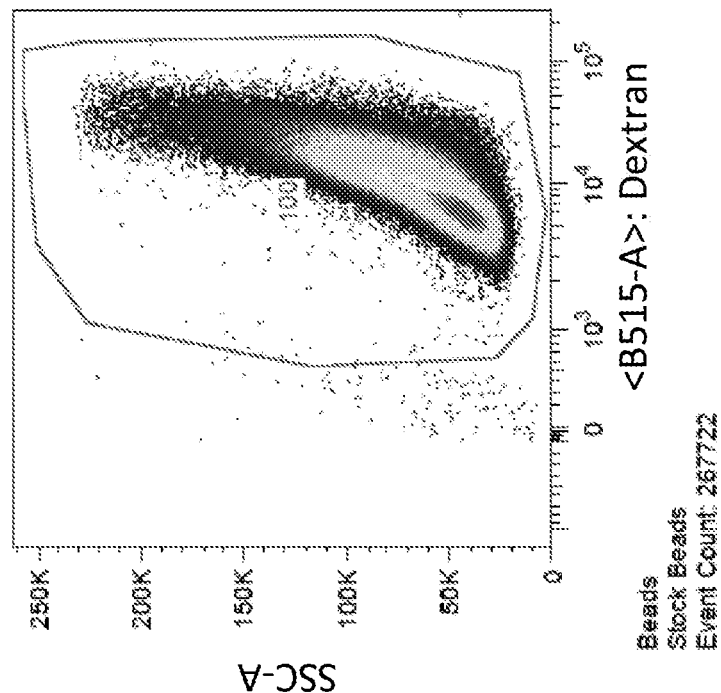
FIG. 1A-1F is a series of histograms showing the number of bead particles by flow cytometry in samples subjected to treatment with or without bleach.

I. Methods and Reagents for Assessing Particles, e.g., Bead Particles

Provided herein are methods for determining or assessing the presence or absence, including the number or concentration, of particles in a sample of a cell composition. In some embodiments, the methods involve incubating a sample of a cell composition that contains or potentially contains non-cell particles (hereinafter called "particles," e.g. bead particles) associated with the cells, wherein the one or more incubations are performed under one or more conditions sufficient to induce lysis of cells in the sample. In some embodiments, the sample comprises at least a portion of a cell composition of interest or a sample derived from a cell composition of interest. In some embodiments, the one or more incubations result in an output composition that is then measured or assessed for the presence or absence of particles (e.g. bead particles). Thus, in the provided methods, an output composition (e.g., sample after the lysis methods) is assessed to determine the presence or absence (e.g. number or concentration) of particles in the sampled cell composition. In some cases, the provided methods permit the efficient and reliable detection of particles (e.g. bead particles) from the cells themselves, thereby improving the accuracy and reliability of visualizing, detecting and/or identifying the particles (e.g. bead particles) in a sample. In some embodiments, the number of particles present in the output composition can be determined using any of a number of methods for visualizing, detecting and/or identifying particles.

In some embodiments, particles (e.g. microspheres or bead particles) and cells can exhibit physical similarities, such as similarities in size, shape and/or color. In some cases, due to the physical similarities between the particles (e.g. microspheres or bead particles) and cells, it can be difficult to assess the particle content in a cell composition comprising cells mixed with particles. In some aspects, in order to detect or determine the presence, absence, number, and/or concentration of particles (e.g. microspheres or bead particles) in a cell composition, methods must be performed to distinguish the cells in the sample from the particles desired to be enumerated.

In some cases, some methods of enumerating particles, such as magnetic bead particles, in a sample include visualization of particles (e.g. bead particles) in a non-lysed cell sample under a microscope. This is possible due to a brown or reddish color of the particles, or other physical characteristic, that differentiates the particles from cells in the sample. When using some particles, such as certain bead particles described herein, this visualization is not possible because at least some of the particles look substantially the same as cells in the sample and so enumerating the particles is not feasible. Further, in a concentrated cell/particle sample, such as provided herein, the number of cells is far greater than the number of particles, further making accurate enumeration of the particles difficult.

In some cases, methods of visualizing or detecting particles requires removing intact cells from the sample, such as methods that lyse or damage the cells in solution, thereby only leaving intact particles to make it easier to visualize individual particles in the sample. Existing methods for removing intact cells include, for example, chemical (e.g. detergent or bleach), thermal and physical lysis methods. For example, previously used methods of lysis or cell damage include, for example, the use of bleach or surfactants. In some aspects, such methods are not entirely satisfactory.

In some cases, use of chemical methods for cell lysis can damage or destroy the particles or otherwise limit the techniques available for detection of the particles due to such damage. For example, in some aspects, such methods can leave large amounts of residual cell debris that can further impair the ability to measure the content, presence, absence, number, and/or concentration of particles (e.g. microsphere or bead particles) in a cell composition. Furthermore, due to the similarity in size between a particle and a cell in the cell composition, it can be hard to determine if visualization of a uniform round body is a particle or a cell that had not been effectively lysed. In some cases, certain cell lysis techniques may not be suitable as they can lead to particle degradation across the cell lysis procedure. Also, another problem with previously employed methods is that such methods often disrupt or destroy the surface or coat of the particles (e.g. bead particles), such as a coat comprising a polysaccharide that is on the surface of a particle. In some cases, damage to the coat of a particle may alter the color observed when the particles are visualized, therefore making such visualization challenging.

It is found herein that such previous methods do not allow accurate enumeration of particles (e.g. bead particles) from a sample comprising cells. In the provided methods, the methods include at least one step of osmotic cell lysis, such as by using a hypotonic solution, to remove intact cells from the sample. In some aspects, one or more further incubations can be performed that can include a further lysis and/or rinse, such as with a hypertonic solution, to remove cell debris, thereby rendering any remaining cell debris sufficiently different from the particles (e.g. bead particles) to allow for accurate particle visualization and enumeration. The presently disclosed methods preserve the integrity of the particle (e.g. bead) surface, rendering the particles compatible for quantification using alternative techniques. Thus, for example, if the surface of the particles (e.g., bead particles) is intact, the particles can be visualized using light microscopy, antibody-based methods (such as FACS), or other methods that rely on an intact bead surface.

Thus, provided herein are methods for assessing the presence or absence of particles in a cell composition comprising a mixture of particles and cells. Such methods allow for the lysis of cells and removal of cellular material in the sample while maintaining consistent particle enumeration during the lysis procedure. The enumerated particles are not damaged by the method, for example, the method does not damage a particle with a coat comprising a polysaccharide. Therefore, the particles obtained by the provided methods are suitable for measurement to assess the absence or presence of particles in a sampled cell composition.

In some embodiments, the provided methods are used to detect the presence or absence of particles, such as bead particles, in a sample that is known to contain or that potentially contains one or more particles (e.g. bead particles). In some embodiments, the sample comprises at least a portion of a cell composition or is derived from a cell composition. In aspects of the method, the sample is a sample that contains a plurality of cells, which plurality of cells is or may be associated with one or more particles (e.g. bead particles). In some embodiments, the provided methods can be used to enumerate or determine the presence, absence, number and/or concentration of the particles (e.g. bead particles) in the sample. In some embodiments, the provided methods offer advantages over existing methods, including those using bleach or detergents, since the provided methods minimize the cellular debris that remains in solution, minimizes the damage to the particle (e.g. microsphere or bead particle) such as coating on the surface of the particle and/or generally improves the consistency and/or precision of enumerating particles throughout the lysis procedure.

In some embodiments, the provided methods involve incubating or contacting a sample containing a plurality of cells under one or more conditions sufficient to induce lysis of cells in the sample, and determining the presence, absence, number and/or concentration of particles (e.g., bead particles) in the sample after lysis of the cells has occurred. In some embodiments, lysis is or includes osmotic lysis (e.g. due to the presence of a hypotonic solution) and/or plasmolysis (e.g. due to the presence of a hypertonic solution). A sample after lysis by the methods described herein, such as by one or more incubation with a hypertonic solution and/or hypotonic solution, is also referred to as an "output composition." As a non-limiting example, the output composition can be a lysed cell composition resulting from one or more incubations of a sample, wherein the one or more incubations of the sample are under a condition sufficient to induce lysis of one or more cells in a sample, thereby producing the output composition. As another non-limiting example, the output composition can be a composition resulting from one or more incubations of a sample to produce a lysed cell composition, wherein the lysed cell composition is further subjected to one or more incubations to reduce or remove the cell debris, thereby producing the output composition. In some embodiments, the one or more lysis and/or incubation conditions are such that they do not or do not substantially interfere with or remove the presence of intact particles in the sample, so that in general, the presence, absence, number and/or concentration of particles in the output composition is the same or substantially the same as the presence, absence number, and/or concentration of particles in the sample prior to the lysis.

In some embodiments, the methods can include the steps of a) performing one or more incubations to produce an output composition, where the one or more incubations in step a) comprises i) incubating a sample of a cell composition that does or potentially does contain particles (e.g. such as a cell composition described herein in Section III) under one or more conditions sufficient to induce lysis (e.g., osmotic lysis and/or plasmolysis) of one or more cells in the sample, thereby producing the output composition; and b) determining the presence, absence, number and/or concentration of particles (e.g. bead particles) in the output composition. In some embodiments, the one or more conditions can include incubating or contacting the sample with a hypotonic solution and/or hypertonic solution.

In some embodiments, the methods can include the steps of a) performing one or more incubations to produce an output composition, where the one or more incubations in step a) comprises i) incubating or contacting a sample of a cell composition that does or potentially does contain particles (e.g. such as a cell composition described herein in Section III) with a hypotonic solution or a hypertonic solution under a condition (e.g., one or more condition) sufficient to induce lysis of one or more cells in the sample, thereby producing a lysed cell composition; ii) incubating or contacting at least a portion of the lysed cell composition with the other of the hypotonic or the hypertonic solution, thereby producing the output composition; and b) determining the presence, absence, number and/or concentration of particles (e.g. bead particles) in the output composition.

In some embodiments, osmotic lysis, such as in the presence of a hypotonic solution, can result in a lysed sample that includes cell debris and/or that may be sticky, for example, due to the release of lipids, DNA and other molecules from the cell. Thus, in some embodiments, after incubating or contacting cells with a hypotonic solution, the method generally includes at least one further step in order to remove cell debris or other components that may impact the ability to detect the number, presence of concentration of the particles (e.g. bead particles). In some embodiments, the further step can include sonication, rinsing or washing of the output composition (which can be a lysed cell composition), an incubation or further incubation of the lysed cell composition with a hypertonic solution or other method to reduce, lessen or remove cell debris in the output composition. In some embodiments, the method is one that is not harsh to the particles (e.g. bead particles) and/or does not destroy the coating or surface of such particles (e.g. bead particles).

In some embodiments, the method generally includes, after incubating or contacting the sample with a hypotonic solution, thereby producing a lysed composition, further incubating or contacting the lysed cell composition with a hypertonic solution to produce the output composition for measurement of particles. Typically, the incubating or contacting with the hypotonic solution is performed prior to the incubating or contacting with the hypertonic solution. In some embodiments, the methods can include the steps of a) performing one or more incubations to produce an output composition, where the one or more incubations in step a) comprises i) incubating or contacting a sample of cell composition that does or potentially does contain particles (e.g. such as a cell composition described herein in Section III) with a hypotonic solution under a condition (e.g., one or more condition) sufficient to induce lysis of one or more cells in the sample, thereby producing a lysed cell composition; ii) incubating or contacting at least a portion of the lysed cell composition with a hypertonic solution, thereby producing the output composition; and b) determining the presence, absence, number, and/or concentration of particles (e.g. bead particles) in the output composition.

In some embodiments, prior to determining or detecting the presence, absence, number, and/or concentration of particles (e.g. bead particles) in the output composition, the method can further include one or more steps for removing or reducing the cell debris in the output composition, such as by performing one or more wash steps or rinse steps of the output composition.

In some embodiments, determining the number of particles (e.g. bead particles) in the output composition can be by any method in which such particles can be visualized, detected, and/or presence, absence, number or concentration determined. In some embodiments, such methods can include microscopy (e.g. using a hemocytometer), flow cytometry and fluorescence-activated cell sorting (FACS), and other affinity-based methods and other methods known to a skilled artisan. Exemplary methods are described below.

In some embodiments, the provided lysis methods are selective to the cells, and thereby do not result in adverse structural or physical damage to the non-cell particles (e.g. microspheres or bead particles). In some cases, the provided lysis methods do not substantially destroy, damage or alter the surface coating of a particle (e.g. microsphere or bead particle). Thus, since the surface of the particle (e.g. microsphere or bead particle) remains relatively intact after the lysis methods, the provided methods permit detection or identification of the surface coating using affinity-based reagents, such as antibody reagents or other binding agents. In some embodiments, the ability to assess, detect or identify particles (e.g. bead particles) by affinity-based methods can result in more reliable results and, in some cases, can be performed in a fraction of the time compared to manual visualization methods, such as using a hemocytometer.

In some embodiments, the method is performed on a sample of cells that is derived from a cell composition or that contains at least a portion of a cell composition. In some embodiments, the cell composition is one that has undergone at least one processing step in the presence of at least one particle (e.g. bead particles) that produces or potentially produces a composition comprising at least one cell specifically associated with at least one particle (e.g. bead particle). In some embodiments, the processing step is or includes one or more of enrichment, separation, selection, isolation, stimulation, activation and/or expansion of the at least one cell in a population or sample of cells.

In some embodiments, the cell composition is one that is intended for use in cell therapy, in which the cell therapy composition contains or potentially contains one or more particles (e.g. bead particles) associated with one or more cells in the composition of cells. As an example, adoptive cell therapy employing immune cells (e.g. T cells) is used a treatment for cancer and other diseases or conditions. In some cases, immune cells (e.g. T cells) to be used in adoptive transfer are obtained from blood or tissue sites and are subsequently engineered with a recombinant receptor that binds to a target antigen associated with the disease or condition prior to reintroduction to the subject. In general, such methods involve selection, isolation, activation and/or expansion of cells using various types of affinity-based particle reagents. For example, use of antibodies against CD3, a multimeric protein complex that serves as a T cell co-receptor to activate T cells, is commonly used in ex vivo T cell proliferation methods for the expansion of T cells along with a costimulatory signal, such as by using anti-CD28 antibodies. When anti-CD3 and anti-CD28 antibodies are immobilized on a surface, they simultaneously deliver a proliferative signal and a costimulatory signal in order to increase T cell proliferation. See Li et al. (2010) J Transl Med., 8:104.

Exemplary methods of processing cells in the presence of particles, such as microspheres or bead particles, that may result or potentially result in a cells associated with at least one such particle is described in Section III. For certain methods, particles (e.g. magnetic bead particles) are used as a surface for immobilization of affinity reagents (e.g. antibodies) for use in various methods, such as in detection, selection, enrichment, isolation, activation and/or stimulation of cells. For example, particles coated with such antibodies have been used as reagents to expand functional T cells for subsequent delivery to a subject, such as by infusion. Particles used for T cell activation and expansion are usually uniformly round-shaped and have about the same size as cells. These particle characteristics can result in some disadvantages in the production and safety of cell adoptive therapy such as T cell adoptive therapy. For example, due to the similarity in size between particles and the cells they have been incubated with, complete removal of the particles from a cell composition comprising a cell population and particles is a significant challenge. The actual number of residual particles left behind in a cell composition after a particle removal process is an important factor to consider when assessing the risk for toxic effects of stimulatory particles that are left behind in a cell composition subsequently used for administration in an individual during cell adoptive therapy. In some embodiments, the process of removing particles (e.g. bead particles, including magnetic beads) after separation from cells can result in a cell composition that may contain residual particles. For example, in some cases where magnetic beads are employed for selection, enrichment and/or activation of cells (e.g. T cells), removal of particles often requires the passing of the cell/bead solution over a magnet. This process can greatly reduce the quantity of particles remaining with the cells (e.g. T-cells), but may not completely eliminate the particles. An incomplete bead removal can result in some particles being infused into patients, which can cause toxic effects. Thus, it is necessary to be able to accurately, reliably and/or efficiently determine or assess the presence or absence of non-cell particles (e.g. bead particles) present in such cell compositions intended for cell therapy.

In some embodiments, after determining the presence, absence, number, and/or concentration of particles in the sample, the method further includes calculating or determining the number of cells present in the cell composition. Thus, in some aspects, the method can provide information about the presence, absence, number, and/or concentration of particles in a larger cell composition from which the sample has been obtained or derived. In some cases, the method can be used to determine or assess if a cell composition is suitable for administration as a cell therapy, such as in connection with adoptive cell therapy methods.

In some embodiments, the provided lysis methods result in a high consistent and/or repeatable enumeration of particles (e.g. microspheres or bead particles) in the sample after the lysis methods (e.g., output composition). In some embodiments, the number of intact particles that do not have a degraded or damaged surface (e.g. intact microsphere or bead particles) in the sample after the lysis methods (e.g., such as in the output composition) is greater than or greater than about 10%, 15%, 20%, 25%, 30%, 35%, 40%, 45%, 50%, 55%, 60%, 65%, 70%, 75%, 80% or 85% as compared to or of the total number of particles and/or expected number of particles in the sample prior to lysis. In some embodiments, the number of intact particles that do not have a degraded or damaged surface (e.g. intact microsphere or bead particles) in the sample after the lysis methods (e.g., such as in the output composition) is greater than or greater than about 85%, 86%, 87%, 88%, 89%, 90%, 91%, 92%, 93%, 94%, 95%, 96%, 97%, 98%, 99% or 100% as compared to the total number of particles and/or expected number of particles in the sample prior to lysis. In some embodiments, the number of particles (e.g. microspheres or bead particles) is generally from or from about 40% to 100%, such as generally greater than 40%, 45%, 50%, 55%, 60%, 65% or 70%. In some embodiments, the repeatable and/or consistent enumeration of particles (e.g. microspheres or bead particles) in a sample by the provided methods is improved compared to other methods that are known or available for enumerating particles (e.g. microspheres or bead particles), such as other methods involving bleach or detergents. In some embodiments, the number and/or concentration of intact particles is at least 1.2-fold, 1.3-fold, 1.4-fold, 1.5-fold, 1.6-fold, 1.7-fold, 1.8-fold, 2-fold, 3-fold, 4-fold, 5-fold or more greater than methods in which the presence, absence, number, and/or concentration of particles in a sample is assessed using a method involving bleach or a detergent.

In some embodiments, by virtue of the improved or greater enumeration of intact particles that do not have a degraded or damaged surface (e.g. intact microspheres or bead particles), the provided methods result in an improved or greater accuracy in detecting or assessing particles in a sample or cell composition compared to other methods. In some embodiments, since the instant methods result in lysis of substantially all or all of the cells in the sample, and optionally removal of residual cell debris, there is a reduced or lower likelihood of a false positive where a cell is counted or identified as a particle. In some embodiments, since the method does not damage the surface of the particle (e.g. microsphere or bead particle), affinity-based methods for detecting or identifying a particle (e.g. using an antibody against a surface marker or coating) can be reliably employed, thereby reducing or minimizing false negatives.

In some embodiments, the precision of the detection or enumeration (e.g., absence of false positives or false negatives) is generally greater than or greater than about 10%, 15%, 20%, 25%, 30%, 35%, 40%, 45%, 50%, 55%, 60%, 65%, 70%, 75%, 80% or 85%. In some embodiments, the precision of the detection or enumeration (e.g., absence of false positives or false negatives) is generally greater than or greater than about 85%, 86%, 87%, 88%, 89%, 90%, 91%, 92%, 93%, 94%, 95%, 96%, 97%, 98%, 99% or 100%. In some embodiments, the precision of detecting or enumerating particles (e.g., microspheres or bead particles) in a cell sample or cell composition is generally from or from about 95% to 100%, such as generally greater than 97%, 98% or 99%. In some embodiments, the precision of detection or enumeration of particles (e.g., microspheres or bead particles) from a cell sample or cell composition by the provided methods is improved (e.g. by at least 1.2-fold, 1.3-fold, 1.4-fold, 1.5-fold, 1.6-fold, 1.7-fold, 1.8-fold, 2-fold, 3-fold, 4-fold, 5-fold or more) compared to other methods that are known or available for enumerating particles, such as other methods involving bleach or detergents.

In some embodiments, the methods can be used to assess or determine if the presence, absence, number, and/or concentration of particles (e.g. microsphere or bead particles) in a cell composition is within an acceptable level or range, such as is or is not greater than a desired threshold or predetermined value. For example, for certain applications or uses of a cell sample or composition, it may not be desirable to have a large number of particles (e.g. microsphere or particle) present in a cell composition. In some cases, even where biodegradable non-cell particles are employed, it may be necessary to monitor or determine the extent, number or presence of such particles in cell compositions used for cell therapies for administration to subjects for treating a disease or condition. In some aspects, a cell composition for cell therapy typically contains no more than 100 particles (e.g. microspheres or bead particles) per $3 \times 10^6$ cells, no more than 75 particles per $3 \times 10^6$ cells, or no more than 50 particles per $3 \times 10^6$ cells. In some aspects, a cell composition for cell therapy typically contains no more than 250 particles per mL, no more than 500 particles per mL, no more than 1000 particles per mL, no more than 2000 particles per mL, or no more than 2500 particles per mL.

In some embodiments, if the method determines that the presence, absence, number, and/or concentration of particles (e.g. microspheres or bead particles) is greater than a predetermined or threshold value for a particular application of a cell composition, the cell composition can be further processed to remove or reduce the number of particles (e.g. microspheres or bead particles) and/or is not released or not validated for use in such application (e.g. cell therapy). In some embodiments, if the method determines that the presence, absence, number, and/or concentration of non-cell particles (e.g. microspheres or bead particles) meets or is below a threshold or predetermined value for a particular application, the cell composition can be released or validated for use in such application (e.g. cell therapy). In some embodiments, for example where it is suspected or known that a certain amount of particles are lost during the sample processing, the threshold can be set to account for a known or suspected bead loss.

II. Incubation(s), Cell Lysis and Detection of Particles

The methods provided herein for detecting the presence, absence, number, amount, or concentration of particles, such as bead particles, include one or more steps of lysing cells in a sample that is known to contain or that potentially contains one or more particles (e.g. bead particles). In some embodiments, the sample contains at least a portion of a cell composition that contains or potentially contains particles, e.g., bead particles. In particular embodiments, the methods provided herein contain one or more steps for determining the presence, absence, number, and/or concentration of particles (e.g. microspheres or bead particles) present in an cell composition, for example, by determining the presence, absence, number, and/or concentration of particles in a sample containing at least a portion of the cell composition. In certain embodiments, the methods provided herein include one or more steps of lysing cells in a sample that is known to contain or that potentially contains one or more particles (e.g. bead particles) and detecting the presence, absence, number, amount, or concentration of particles in the sample.

A. Incubation and Cell Lysis

In some embodiments, the cells in a sample comprising at least a portion of a cell composition that does or potentially does contain particles (e.g. such as a cell composition described herein in Section III) or a sample derived from such a cell composition are mixed, incubated, contacted or re-suspended to expose the cells to a condition (e.g., one or more condition) sufficient to induce lysis of cells in the sample. In some embodiments, the sample of cells is provided as a suspension of cells and the method includes subjecting the suspension of cells to one or more conditions that induces lysis of the cells. In some embodiments, the lysis method is one that maintains the particles intact, such that the particles can be easily identified, visualized and/or detected. In some embodiments, the lysis method does not destroy the coating or the surface of the particles, which, in some cases, can facilitate their detection.

In some cases, the one or more condition induces osmotic lysis of the cells in the sample. In some embodiments, the method involves mixing, incubating, exposing, contacting or resuspending a sample of cells that does or that may contain one or more particles (e.g., microsphere or bead particles) with one or more conditions that create a change in osmotic pressure in the cells, resulting in an osmotic imbalance that causes water to transfer into the cell so that a substantial number of cells in the sample lyse. A variety of known techniques can be used to create a change in an osmotic pressure in the cells. In some aspects of the method, a sample of cells is provided and osmotic lysis is induced by mixing, incubating, exposing, contacting or resuspending the cells with a hypotonic solution to result in a hypotonic cell suspension having an osmolarity that is reduced to less than the osmolarity of the inside of the cells, such as generally to less than the physiological osmolarity. Typically, the physiological osmolarity to which cells are exposed is approximately 290 mOsm/L to 300 mOsm/L. In general, cell culture media and other cell buffers are designed to maintain an osmolarity of between 270 mOsm/L and 330 mOsm/L, such as to mimic the physiological osmolarity of serum. Thus, changes in the osmolarity caused by exposure of cells to the hypotonic solution, and the resulting changes in osmotic pressure in the cells mixed, contacted or suspended in the solution, can lead to lysis of substantially all of the cells in the composition, while leaving the particles (e.g., bead particles) intact.

In some aspects, cells typically lyse due to osmotic pressure if the total volume of the cell swells to approximately 150% of the original volume, although the percentage may vary somewhat with cell type and other factors (Kinosita et al. (1977) Proc. Natl. Acad. Sci., 74:1923-7). In some embodiments, the method includes subjecting a sample, such as a suspension of cells having a standard osmolarity (e.g. 270 mOsm/L-330 mOsm/L), to a hypotonic solution such that the osmolarity of the hypotonic cell suspension is sufficiently reduced so that the total volume expansion of the cells in the suspension exceeds about 150% of the volume of the cell when under standard physiological osmolarity conditions. In general, the particular osmolarity of the hypotonic solution to effect a reduction in osmolarity of the resulting hypotonic cell suspension can be empirically determined, such as based on the particular cell type or cell types in the sample, the density of cells in the sample, the volume of the resulting hypotonic cell suspension, the length of incubation, the temperature of incubation and other factors known to a skilled artisan. In some cases, cells with small nuclear to cell diameter ratios can lyse at osmolarities that are much higher than cells where the nuclear to cell diameter is greater (published PCT Appl. No. WO1999054439).

In some embodiments, a hypotonic solution is added to a solution-free cell sample, for example as obtained after centrifugation of the cells into a pellet and discarding of the supernatant or after collection of the cells on a filtration membrane. Alternatively, the solution-free cell sample (or a fraction thereof) may be added to the hypotonic solution. In both cases above, the hypotonic solution can be mixed with the cells to result in a hypotonic cell suspension in which the cells are suspended under hypotonic conditions. In some embodiments, a predetermined volume of a hypotonic solution is added to cells suspended in a standard physiological osmolarity solution (e.g. standard cell media or buffer) to form the hypotonic cell suspension. In such embodiments, a predetermined volume of the hypotonic solution having a predetermined osmolarity is dispensed into, such as mixed with, the cell suspension (or, equivalently, the cell suspension may be dispensed or mixed into the hypotonic solution) in order to result in a hypotonic cell suspension with a reduced osmolarity compared to the osmolarity of the initial suspension of cells.

In some embodiments, the hypotonic solution is any liquid that can be mixed with cells or a cell suspension to effect a change in osmotic pressure in the cells. In some embodiments, the hypotonic solution can include, but is not limited to, a solution containing one or more solutes in a solvent or mixture of solvents, generally pure solvents (e.g. distilled deionized water), or mixtures of essentially pure solvents, so long as the hypotonic solution has an osmolarity that is different from an osmolarity of the cells to which it is contacted, mixed or suspended. In general, the hypotonic solution is one that, when contacted, mixed or suspended with cells or a cell suspension, can result in a suspension of cells that has a solution osmolarity that is hypotonic.

In some embodiments, the hypotonic solution is solute-free. In some embodiments, the hypotonic solution can be sterile water for injection, such as distilled/deionized water (DDI water).

In some embodiments, the hypotonic solution is or can be formulated in the presence of solutes. In some embodiments, the concentration of solute present in the hypotonic solution is such that the osmolarity of the hypotonic solution or the osmolarity of the resulting hypotonic cell suspension is less than the physiological osmolarity, such as generally less than 270 mOsm/L. In some cases, the solute or solutes that can be present include any that may be present in standard reagents, such as in standard cell media or buffers. In some embodiments, the solutes in a hypotonic solution can include salts such as sodium chloride (NaCl), ammonium chloride, potassium chloride, sodium citrate, and sugars such as dextrose, glucose and sucrose. In some embodiments, a solute can be one that is provided or present in standard media, such as phosphate buffered saline (PBS), Iscove's Modified Dulbecco's Medium (IMDM) and other standard cell culture media, which generally have a standard physiological osmolarity of about 300 mOsm/L. In some embodiments, a hypotonic solution can be obtained by dilution of a solute-providing media or buffer, such as PBS or IMDM, with a solvent. In some cases, distilled/deionized water can be used as the solvent for such dilution. The pH of the hypotonic solution can be adjusted as needed, generally to a pH that does not damage the particles described herein.

In some embodiments, the hypotonic solution comprises a solute concentration of between or between about 0 mM and 140 mM. In some embodiments, the hypotonic solution comprises a solute concentration of less than or about less than 140 mM, 100 mM, 50 mM or 10 mM.

In some embodiments herein, the hypotonic solution comprises a weight percent (% w/v) of solute of between about 0% and about 0.8% or between about 0% and about 0.5%. In some embodiments, the hypotonic solution comprises a weight percent (% w/v) of solute of less than about 0.8%, less than about 0.7%, less than about 0.6%, less than about 0.5%, less than about 0.4%, less than about 0.3% or less than about 0.2%.

In some of the embodiments, the hypotonic solution or resulting hypotonic cell suspension has an osmolarity between about 0 mOsm/L and about 270 mOsm/L, such as between about 0 mOsm/L and 200 mOsm/L, 0 mOsm/L and 140 mOsm/L, 0 mOsm/L and 100 mOsm/L, 10 mOsm/L and 200 mOsm/L, 10 mOsm/L and 140 mOsm/L, 10 mOsm/L and 100 mOsm/L, 50 mOsm/L and 200 mOsm/L, 50 mOsm/L and 140 mOsm/L, 50 mOsm/L and 100 mOsm/L, 100 mOsm/L and 200 mOsm/L, 100 mOsm/L and 140 mOsm/L or 140 mOsm/L and 200 mOsm/L. In some embodiments, the hypotonic solution or resulting hypotonic cell suspension has an osmolarity of less than about 270 mOsm/L, less than about 250 mOsm/L, less than about 225 mOsm/L, less than about 200 mOsm/L, less than about 175 mOsm/L, less than about 150 mOsm/L, less than about 140 mOsm/L, less than about 125 mOsm/L, less than about 100 mOsm/L, less than about 75 mOsm/L, less than about 50 mOsm/L, less than about 25 mOsm/L or less than about 10 mOsm/L.

In some embodiments, since osmotic lysis is driven by the solute concentration difference across a cell's membrane, the extent of lysis can be related to the time of incubation of cells under hypertonic conditions. In some embodiments, the provided method involves one or more incubation (e.g., one, two, three, etc. incubations) of the hypotonic cell suspension for a sufficient time in which substantially all of the cells are lysed, such as generally greater than 90%, 91%, 92%, 93%, 94%, 95%, 96%, 97%, 98%, 99% or up to 100% of the cells are lysed. In some embodiments, after mixing, combining or suspending the cells or cell suspension with a hypotonic solution, the resulting hypotonic cell suspension is incubated from or from about 30 seconds to 5 hours, such as 30 seconds to 30 minutes, 1 minute to 20 minutes, 1 minute to 10 minutes, 1 minute to 5 minutes, 15 minutes to 3 hours, 15 minutes to 2 hours, 15 minutes to 1 hour, 15 minutes to 30 minutes, 30 minutes to 3 hours, 30 minutes to 2 hours, 30 minutes to 1 hour, 1 hour to 3 hours, 1 hour to 2 hours or 2 hours to 3 hours. In some embodiments, after mixing, combining or suspending the cells or cell suspension with a hypotonic solution, the resulting hypotonic cell suspension is incubated for at least or at least about 30 seconds, at least or at least about 1 minute, at least or at least about 2 minutes, at least or at least about 3 minutes, at least or at least about 4 minutes, at least or at least about 5 minutes, at least or at least about 10 minutes, at least or at least about 15 minutes, at least or at least about 20 minutes, at least or at least about 30 minutes, at least or at least about 1 hour, at least or at least about 2 hours or at least or at least about 3 hours. In some embodiments, during the one or more incubation, the cells can be mixed or gently shaken in order to maintain the cells in a suspension or mixture with the hypotonic solution.

In some embodiments, the lysis (e.g., osmotic lysis), such as during one or more incubations of a hypotonic cell suspension, is performed at a temperature of from or from about 0° C. to 50° C. In some embodiments, one or more incubations of cells or a cell suspension or lysed cell composition (e.g., previously lysed in the presence of a hypotonic solution and/or hypertonic solution) with a hypotonic solution, is performed at a temperature of from or from about 0° C. to 50° C. In some embodiments, the temperature can be at or with a particular range associated with refrigerated temperatures (e.g. 2° C. to 8° C.), ambient temperature (e.g. 16° C. to 25° C.) or physiological temperature (e.g. 35° C. to 38° C.). In some embodiments, the temperature is about 15° C. to about 30° C., about 18° C. to about 28° C. or about 20° C. to about 25° C. In some embodiments, the temperature is at least or at least about or is or is about 4° C.±2° C., 23° C.±0.2° C., 25° C.±2° C., or 37° C.±2° C.

In some embodiments, cell swelling leading to lysis can result in release of cellular intracellular constituents (e.g. DNA, cytoplasm) that can alter the effective osmolarity of the hypotonic cell suspension, particularly over the length of the incubation. In some cases, if the cell density is very high, the release of such intracellular species can alter the effective osmolarity of the hypotonic cell suspension. In some embodiments, the hypotonic solution is combined, mixed or used to resuspend cells in the sample to result in a hypotonic cell suspension in which the cell density is less than or less than about $2\times10^7$ cells/mL, less than or less than about $1\times10^7$ cells/mL, less than or less than about $5\times10^6$ cells/mL, less than or less than about $1\times10^6$ cells/mL, less than or less than about $5\times10^5$ cells/mL or less than or less than about $1\times10^5$ cells/mL. In some embodiments, the hypotonic cell suspension has a density that is between or between about $1\times10^2$ cells/mL and $2\times10^7$ cells, such as $1\times10^4$ cells/mL to $1\times10^7$ cells/mL, $1\times10^4$ cells/mL to $1\times10^6$ cells/mL, or $1\times10^6$ cells/mL to $2\times10^7$ cells/mL.

In some embodiments, the volume of the hypotonic cell suspension that is incubated is 1 mL to 1000 mL, such as 1 mL to 500 mL, 1 mL to 250 mL, 1 mL to 100 mL, 1 mL to 50 mL, 1 mL to 10 mL, 1 mL to 5 mL, 5 mL to 500 mL, 5 mL to 250 mL, 5 mL to 100 mL, 5 mL to 50 mL, 5 mL to 10 mL, 10 mL to 500 mL, 10 mL to 250 mL, 10 mL to 100 mL, 10 mL to 50 mL, 50 mL to 500 mL, 50 mL to 250 mL, 50 mL to 100 mL, 100 mL to 500 mL, 100 mL to 250 mL or 250 mL to 500 mL. In some embodiments, the volume of the hypotonic cell suspension is at least or about at least 1 mL, 5 mL, 10 mL, 25 mL, 50 mL, 75 mL, 100 mL, 200 mL, 300 mL, 400 mL or 500 mL. In some embodiments, volumes for reagents (e.g., hypotonic solution) can be adjusted as needed to optimize cell lysis as needed. For instance, when higher cell numbers are used, the reagent volumes and total volumes can be scaled up accordingly.

In some embodiments, additionally or alternatively, the one or more conditions to induce lysis of cells in the sample includes any that induces or causes plasmolysis of cells in the sample and/or involves mixing, incubating, exposing, contacting or resuspending cells or a cell suspension with a hypertonic solution. In some embodiments, a hypertonic solution can cause the lysis (death by internal bursting) of one or many cells by causing the cells to swell from abnormal osmosis and putting too much pressure upon the internal walls of the cell that then bursts, and thus dies. In some embodiments, the method includes subjecting a sample, such as a sample comprising a suspension of cells, to a hypertonic solution that has an osmolarity that is greater or higher than the inside of the cells or cell suspension prior to incubation or contacting with the hypertonic solution, thereby causing the cell to swell from abnormal osmosis leading to internal bursting. In general, the particular osmolarity of the hypertonic solution to effect an increase in osmolarity of the resulting hypertonic cell suspension can be empirically determined, such as based on the osmolarity of the cell or cell suspension prior to contacting or incubation with the hypertonic solution (e.g. if the cell or cell suspension has been previously incubated or contacted with a hypotonic solution), the particular cell type or cell types in the sample, the density of cells in the sample, the volume of the resulting hypertonic cell suspension, the length of incubation, the temperature of incubation and other factors known to a skilled artisan.

In some embodiments, the one or more incubations to induce cell lysis (e.g. by incubation with a hypotonic solution) results in a lysed cell composition that can be directly assessed as the output composition for measuring, determining or assessing the presence, absence, number or concentration of particles in the sample. In other embodiments, the lysed cell composition is further processed by one or more additional incubations, rinses and/or washes prior to obtaining a resulting output composition for measuring, determining or assessing the presence, absence, number or concentration of particles in the sample. For example, in some cases, incubation of a cell sample with a hypotonic solution can lead to a hypotonic lysis that can generate cellular debris that can interfere with the determination of the presence or number of particles in the lysed cell composition. In some embodiments, after the hypotonic lysis, the method can further include reducing, lessening or removing cell debris in the hypotonic lysed cell composition prior to determining the presence, absence, number, and/or concentration of particles (e.g. bead particles or microspheres) present in the lysed sample.

In some embodiments, incubation with a hypertonic solution can be employed in the context of the provided method to reduce, lessen or remove cell debris in a lysed cell composition described herein. In some embodiments, reducing or removing cell debris in a lysed cell composition can include: i) contacting or incubating the lysed cell composition, such as a hypotonic lysed cell composition, in the presence of a hypertonic solution, thereby producing the output composition; and ii) rinsing or washing the output composition, wherein cell debris is reduced or removed. In some embodiments, provided herein is a method of detecting the presence or absence of particles (e.g. bead particles or microspheres) in a sample of a cell composition, such as to enumerate particles in the cell composition, that includes: i) incubating or contacting a sample with a hypotonic solution, thereby producing a lysed cell composition (or hypotonic lysed cell composition); ii) incubating or contacting the lysed cell composition with a hypertonic solution, thereby producing an output composition; iii) optionally rinsing or washing the output composition; and determining the presence, absence, number, and/or concentration of particles (e.g. microspheres or bead particles) in the output composition or the washed/rinsed output composition.

In some embodiments, a hypertonic solution is added to a solution-free cell sample, for example as obtained after centrifugation of the cells into a pellet and discarding of the supernatant or after collection of the cells on a filtration membrane. Alternatively, the solution-free cell sample (or a fraction thereof) may be added to the hypertonic solution. In both cases above, the hypertonic solution can be mixed with the cells to result in a hypertonic cell suspension in which the cells are suspended under hypertonic conditions. In some embodiments, the hypertonic cell suspension is formed by adding a predetermined volume of a hypertonic solution to a cell suspension having a lower osmolarity, such as cells suspended in a standard physiological osmolarity solution (e.g. standard cell media or buffer) or cells suspended in a hypotonic solution (e.g. a hypotonic lysed cell composition). In such embodiments, a predetermined volume of the hypertonic solution having a predetermined osmolarity is dispensed into, such as mixed with, the cell suspension (or, equivalently, the cell suspension may be dispensed or mixed into the hypertonic solution) in order to result in a hypertonic cell suspension with an increased or greater osmolarity compared to the osmolarity of the initial suspension of cells prior to the addition of the hypertonic solution.

In some embodiments, the osmolarity of a hypertonic solution is greater than the physiological osmolarity of a cell, such as is generally greater than or greater than about 300 mOsm/L. In some embodiments, the hypertonic solution can be any solution that has a greater concentration of solute as compared to the inside of the cell. In some embodiments, a hypertonic solution has an appropriate concentration of a solute that is effective at reducing or removing cell debris in a lysed cell composition.

In some embodiments, a solute for use in a hypertonic solution includes, but is not limited to, salts such as sodium chloride (NaCl), ammonium chloride, potassium chloride, sodium citrate, and sugars such as dextrose, glucose and sucrose. In some embodiments, a hypertonic solution for use in a method described herein can comprise one or more of sodium chloride, ammonium chloride, potassium chloride, or sodium citrate. In some embodiments, the hypertonic solution comprises sodium chloride. In some embodiments, the hypertonic solution comprises sucrose. Hypertonic solutions may comprise further agents such as, but not limited to, buffering agents (e.g., HEPES) and protease inhibitors. The pH of the hypertonic solution can be adjusted as needed, preferably to a pH that does not damage the non-cell particles (e.g. microspheres or bead particles) described herein.

In some embodiments, the hypertonic solution comprises a weight percent (% w/v) of solute of between about 1.5% and about 15% or between about 2.5% and about 12%. In some embodiments, the hypertonic solution comprises a weight percent (% w/v) of solute of greater than about 1.5%, greater than about 2.5%, greater than about 3.0%, greater than about 3.5%, greater than about 4.0%, greater than about 4.5%, greater than about 5.0%, greater than about 5.5%, greater than about 6.0%, greater than about 6.5%, greater than about 7.0%, greater than about 7.5%, greater than about 8.0%, greater than about 8.5%, greater than about 9.0%, or greater than about 9.5% but no more than about 10.0%.

In some embodiments, the hypertonic solution has an osmolarity of between about 300 mOsm/L and about 5000 mOsm/L, between about 300 mOsm/L and about 4000 mOsm/L, between about 300 mOsm/L and about 3000 mOsm/L, between about 300 mOsm/L and about 2000 mOsm/L, between about 300 mOsm/L and about 1000 mOsm/L, between about 1000 mOsm/L and about 5000 mOsm/L, between about 1500 mOsm/L and about 5000 mOsm/L, between about 2000 mOsm/L and about 5000 mOsm/L, between about 2500 mOsm/L and about 5000 mOsm/L, between about 3000 mOsm/L and about 5000 mOsm/L, between about 3500 mOsm/L and about 5000 mOsm/L, between about 4000 mOsm/L and about 5000 mOsm/L, between about 1000 mOsm/L and about 3000 mOsm/L, or between about 1000 mOsm/L and about 2000 mOsm/L or between about 1800 mM and about 2000 mM.

In some embodiments, the hypertonic solution has an osmolarity greater than about 300 mOsm/L, greater than about 400 mOsm/L, greater than about 500 mOsm/L, greater than about 600 mOsm/L, greater than about 700 mOsm/L, greater than about 800 mOsm/L, greater than about 900 mOsm/L, greater than about 1000 mOsm/L, greater than about 1200 mOsm/L, greater than about 1400 mOsm/L, greater than about 1500 mOsm/L, greater than about 1600 mOsm/L, greater than about 1800 mOsm/L, greater than about 2000 mOsm/L, greater than about 2500 mOsm/L, greater than about 3000 mOsm/L, or greater than about 4000 mOsm/L.

In some embodiments, after mixing, combining or suspending the cells or cell suspension or lysed cell composition (e.g. previously lysed in the presence of a hypotonic solution) with a hypertonic solution, the resulting hypertonic cell suspension composition is incubated from or from about 30 seconds to 5 hours, such as 30 seconds to 30 minutes, 1 minute to 20 minutes, 1 minute to 10 minutes, 1 minute to 5 minutes, 15 minutes to 3 hours, 15 minutes to 2 hours, 15 minutes to 1 hour, 15 minutes to 30 minutes, 30 minutes to 3 hours, 30 minutes to 2 hours, 30 minutes to 1 hour, 1 hour to 3 hours, 1 hour to 2 hours or 2 hours to 3 hours. In some embodiments, after mixing, combining or suspending the cells or cell suspension or lysed composition (e.g. previously lysed in the presence of a hypotonic solution) with a hypertonic solution, the resulting hypertonic cell suspension is incubated for at least or at least about 30 seconds, at least or at least about 1 minute, at least or at least about 2 minutes, at least or at least about 3 minutes, at least or at least about 4 minutes, at least or at least about 5 minutes, at least or at least about 10 minutes, at least or at least about 15 minutes, at least or at least about 20 minutes, at least or at least about 30 minutes, at least or at least about 1 hour, at least or at least about 2 hours or at least or at least about 3 hours. In some embodiments, during the incubation, the cells can be mixed or gently shaken in order to maintain the cells in a suspension or mixture with the hypertonic solution.

In some embodiments, contacting or incubating cells or a cell suspension or lysed cell composition (e.g., previously lysed in the presence of a hypotonic solution) with a hypertonic cell solution, is performed at a temperature of from or from about 0° C. to 50° C. In some embodiments, the temperature can be at or with a particular range associated with refrigerated temperatures (e.g., 2° C. to 8° C.), ambient temperature (e.g., 16° C. to 25° C.) or physiological temperature (e.g., 35° C. to 38° C.). In some embodiments, the temperature is about 15° C. to about 30° C., about 18° C. to about 28° C. or about 20° C. to about 25° C. In some embodiments, the temperature is at least or at least about or is or is about 4° C.±2° C., 23° C.±0.2° C., 25° C.±2° C., or 37° C.±2° C.

In some embodiments, the volumes of the hypertonic solution can be chosen or adjusted as needed to optimize cell lysis and/or removal of cell debris from the lysed cell compositions described herein. For instance, when higher cell numbers are used, the reagent volumes and total volumes can be scaled up accordingly. In some embodiments, the volume of the hypertonic cell suspension that is incubated is 1 mL to 1000 mL, such as 1 mL to 500 mL, 1 mL to 250 mL, 1 mL to 100 mL, 1 mL to 50 mL, 1 mL to 10 mL, 1 mL to 5 mL, 5 mL to 500 mL, 5 mL to 250 mL, 5 mL to 100 mL, 5 mL to 50 mL, 5 mL to 10 mL, 10 mL to 500 mL, 10 mL to 250 mL, 10 mL to 100 mL, 10 mL to 50 mL, 50 mL to 500 mL, 50 mL to 250 mL, 50 mL to 100 mL, 100 mL to 500 mL, 100 mL to 250 mL or 250 mL to 500 mL. In some embodiments, the volume of the hypertonic cell suspension is at least or about at least 1 mL, 5 mL, 10 mL, 25 mL, 50 mL, 75 mL, 100 mL, 200 mL, 300 mL, 400 mL or 500 mL.

In some embodiments herein, after performing the lysis (e.g. hypotonic and/or hypertonic lysis), the output composition is processed to wash, rinse and/or separate the particles (e.g. microspheres or bead particles) from other material or debris that may be present in the cell composition. In some embodiments, after performing the lysis (e.g. hypotonic and/or hypertonic lysis), the output composition is processed to pellet, if present, any particles (e.g. microspheres or bead particles) in the output composition. Methods for pelleting particles in compositions are well known in the art. In some embodiments, an output composition can be spun in a centrifuge at a centrifugation speed sufficient to pellet, if present, any particles. In some embodiments, the centrifugation speed is sufficient to pellet the particles (e.g. microspheres or bead particles) without damaging such particles. In some embodiments, the centrifugation speed can be adjusted to take into account the model of the centrifuge and/or centrifuge rotor radius. In some embodiments, centrifugation is at a speed of from or from about 200×g to 1000×g, such as generally at least or about at least 400×g, 450×g, 500×g or 600×g. The centrifugation can proceed for a time sufficient to pellet the particles. In some embodiments, the output composition is centrifuged from 1 minutes to 60 minutes, such as generally 1 minute to 30 minutes, 1 minute to 15 minutes or 1 minute to 5 minutes, for example, at least or at least about 1 minute, 2 minutes, 3 minutes, 4 minutes, 5 minutes, 6 minutes, 7 minutes, 8 minutes, 9 minutes, 10 minutes, 15 minutes or 30 minutes.

In some embodiments, after pelleting, the volume of the output composition can be adjusted as desired, such as by completely or partially removing the supernatant solution. In some embodiments, after pelleting, all or substantially all of the supernatant can be removed and replaced with fresh buffer or media to a desired volume. In general, the buffer or media can be any that is compatible with the particles and/or does not interfere with subsequent visualization or detection of the particles. In other embodiments, after pelleting, the volume of the output composition can be reduced (e.g., by removing a volume of the supernatant in the centrifuged output composition or reducing the volume or the total centrifuged output composition) to a desired volume prior to determining the presence or number of particles (e.g. microspheres or bead particles). In some embodiments, the volume of the output composition can be reduced by less than about 100% but greater than about 50%, about 60%, about 70%, about 80%, about 90% or about 95% compared to the volume of the output composition prior to the pelleting (e.g. centrifugation).

In some embodiments, replacing, reducing or removing supernatant from the output composition effects rinsing or washing of the output composition prior to determining the presence, absence, number, and/or concentration of particles (e.g., bead particles). In some embodiments, replacing, reducing or removing supernatant from the output composition effects concentration or dilution (as appropriate) of the output composition prior to determining the presence, absence, number, and/or concentration of particles. In some embodiments, the steps of pelleting (e.g. by centrifugation) and replacing, washing or removing supernatant of the output composition can be repeated a plurality of times.

In some embodiments, the total volume of the output composition after replacing, reducing or removing supernatant is a volume that permits detection of the particles in the sample (e.g. not too concentrated). In some embodiments, the desired volume is about the same or is the same as the sample prior to the one or more incubations of the methods. In some embodiments, the volume is from or from about 0.25 mL to 50 mL, such as from or from about 0.5 mL to 50 mL, 0.5 mL to 25 mL, 0.5 mL to 10 mL, 0.5 mL to 5 mL, 0.5 mL to 1 mL, 1 mL to 50 mL, 1 mL to 25 mL, 1 mL to 10 mL, 1 mL to 5 mL, 5 mL to 50 mL, 5 mL to 25 mL, 5 mL to 10 mL, 10 mL to 50 mL, 10 mL to 25 mL or 25 mL to 50 mL. In some embodiments, the volume is at least or at least about or 0.5 mL, 1 mL, 1.5 mL, 2 mL, 3 mL, 4 mL, 5 mL, 6 mL, 7 mL, 8 mL, 9 mL, 10 mL, 15 mL, 20 mL, 30 mL, 40 mL or 50 mL.

B. Methods of Counting Particles

In some embodiments, the presence, absence, number, and/or concentration of particles (e.g. microspheres or bead particles) present in an output composition is determined. Methods for determining the presence of (e.g. concentration or number) and/or detecting particles in an output composition, e.g., a sample after the lysis methods have been performed, can be performed using techniques well known in the art. In some embodiments, methods for determining the presence, absence, number, and/or concentration of particles (e.g. microspheres or bead particles) in an output composition can include manual counting, electronic counting, microscopy (e.g., fluorescent microscopy), affinity-based detection, or sorting (e.g., magnetic bead sorting). Techniques for use in such methods include, but are not limited to, flow cytometry (e.g., fluorescence-activated cell sorting (FACS)), spectrophotometry, microscopy such as bright field microscopy (e.g., using a hemocytometer), phase contrast microscopy, fluorescent microscopy, and electron microscopy, and biosensor arrays. See Giouroudi et al., Int J Mol Sci., 2013, 14(9):18535-18556.

In some embodiments, the technique can be manual or automated.

In some cases, a particle count (e.g., bead count) can be obtained using such techniques and the particle count can be repeated. After the particle count is repeated, the obtained particle counts can be averaged and a standard deviation can be determined.

In some embodiments, the output composition, such as the output composition produced in step a) of the methods described herein, can be prepared by one or more processing steps prior to determining the presence, absence, number, and/or concentration of particles in step b) of the methods described herein. In some cases, the one or more processing steps of the output composition involve separation, centrifugation, washing, and/or incubation.

In some embodiments, the output composition is incubated with a reagent that detects the particles. In some embodiments, an affinity based method or technique can be used to detect and/or enumerate the particles in step b) of the methods described herein. In some aspects, the provided methods do not alter or substantially alter any materials, moieties or molecules attached to, present or otherwise associated with the particles, thereby permitting direct or indirect detection of such materials, moieties or molecules using a binding agent (e.g. antibody, ligand or other binding molecule) that specifically binds or recognizes such material, moiety or molecule. In some embodiments, the binding agent is an antibody or an antigen-binding fragment thereof. For example, the binding agent may be an antibody or antigen-binding fragment thereof that recognizes a material on the particle, such as a polysaccharide (e.g., dextran, amino-dextran, etc.) on the coating of a particle, a biomolecule (e.g. antibody) attached to a particle or other material or moiety present on and/or associated with the particle. In some embodiments, the extent or level of detection by the binding agent of a material on or associated with the particle and/or a biomolecule attached to the particle in particles of an output composition, on average, is at least or about at least 50%, 60%, 70%, 75%, 80%, 85%, 90%, 95% or more the extent or level of detection of the same material or biomolecule by the binding agent, on average, in a reference composition that comprises substantially the same or the same particles but that was not exposed or subjected to the one or more incubations in accord with the provided methods. In some embodiments, the extent or level of detection by a binding agent of a material on or associated with the particle and/or a biomolecule attached to the particle in particles of an output composition, on average, is about or about at least 2-fold, 3-fold, 4-fold, 5-fold, 6-fold, 7-fold, 8-fold, 9-fold, 10-fold, 20-fold, 30-fold, 40-fold, 50-fold or more greater than the extent or level of detection of the same material or biomolecule by the binding agent, on average, in a reference composition comprising substantially the same or the same particles but that has been treated with bleach instead of subjected to the one or more incubations in accord with the provided method.

In some embodiments, the binding agent binds to a polymer, a polysaccharide, a silica, a fatty acid, and/or a carbon on the particle, such as on the coating of the particle. In some embodiments, the binding agent can be an antibody or antigen-binding fragment thereof that binds to the polysaccharide present on the particle coat. In some embodiments, the polysaccharide can be dextran or amino-dextran and the binding agent can be an anti-dextran antibody or anti-amino-dextran antibody or antigen-binding fragments thereof. In some embodiments, the binding agent binds to a biomolecule conjugated, linked and/or coupled to the particle, such as to a biomolecule conjugated, linked and/or coupled to the coating of the particle. In some embodiments, the biomolecule is a nucleic acid (e.g., DNA), protein, antibody or antigen-binding fragment thereof, antigen, or any other biomolecule as described herein.

In some embodiments, the binding agent can be one that detects a biomolecule attached to the particle. In some embodiments, the biomolecule is an antibody (e.g. anti-CD3 and/or anti-CD28 antibody or other as described herein or known in the art). In some embodiments, the binding agent for detecting the biomolecule (e.g. antibody) is an anti-idiotypic antibody against an antibody on the surface of the particle. In some embodiments, the binding agent for detecting the biomolecule (e.g. antibody) is an anti-isotypic antibody against a class, subclass, type or subtype of the heavy or light chain of the antibody. In some embodiments, the binding agent is an antibody that recognizes or specifically binds an IgG class, such as directed against IgG1, IgG2a, IgG2b, IgG3 or IgG4. In some embodiments, the biomolecule is an antibody that is a mouse, rabbit, rat, goat, sheep, donkey or human antibody and the binding agent recognizes such species (e.g. the biomolecule is a mouse antibody and the affinity reagent is an anti-mouse IgG1, anti-mouse IgG2a, etc.).

In some embodiments, the binding agent may be labeled such as with a florescent dye, a fluorescent protein, a gold particle, a silver particle, particles with different scattering spectra as compared to the particles in the output composition, polypeptides (e.g., FLAG™ tag, human influenza hemagglutinin (HA) tag, etc.), enzymes, streptavidin, biotin, chemiluminescent substrates, and other labels well known the art that are used for visualizing or detecting an affinity reagent bound to its target.

In some embodiments, provided is a method of enumerating or detecting the presence or absence of particles in a cell composition, wherein the method comprises the steps of a) performing one or more incubations, thereby producing an output composition, wherein the one or more incubations in step a) comprises i) incubating a sample comprising at least a portion of a cell composition or a sample derived from the cell composition, under a condition sufficient to induce lysis of one or more cells in the sample, wherein the particle comprises a coat and/or one or more biomolecules attached to the coat or particle, and b) determining the presence, absence, number and/or concentration of particles in the output composition using a binding agent that specifically binds to the material on surface of the particle (e.g. polysaccharide) and/or a biomolecule attached to the particle, thereby enumerating or detecting the presence or absence of particles in the cell composition. In some embodiments, the binding agent is an antibody or antigen-binding fragment thereof. In some embodiments, the particle comprises a coat containing dextran and the binding agent is an anti-dextran antibody. In some embodiments, the particle comprises a coat containing an antibody (e.g., mouse antibody) and the binding agent is an antibody (e.g., anti-mouse antibody). In some embodiments, the particle comprises a coat containing streptavidin and the binding agent is an anti-streptavidin antibody or a biotinylated molecule.

As an example of the one or more processing steps, the output composition may comprise particles, wherein one or more of the particles further comprises a coat that contains a polysaccharide (e.g. dextran) and/or one or more antibody biomolecules against a cell surface protein (e.g. anti-CD3, anti-CD28 or other antibody biomolecule). In some embodiments, the output composition is washed and/or centrifuged to remove or reduce cell debris. The output composition may subsequently be incubated with a binding agent (e.g., fluorescently labeled anti-dextran antibody) that recognizes a polysaccharide (e.g., dextran) and/or a binding agent (e.g. fluorescently labeled anti-isotypic antibody) that recognizes an antibody biomolecule (e.g. anti-CD3 or anti-CD28) under a condition sufficient to allow the binding agent to bind the polysaccharide or biomolecule. The output composition can be incubated with a blocking solution, such as a solution comprising a protein such as human serum albumin. In some cases, the blocking solution aids in preventing non-specific binding by the binding agent to other components of the cell composition. In some embodiments, the output composition may be incubated with the blocking solution, prior to, concurrently with or subsequently to the incubation with the binding agent. The output composition may be further washed and/or centrifuged to remove excess binding agent and/or binding agent that is not specifically bound to the polysaccharide or biomolecule on the particle.

In some embodiments, the binding agent allows for detection of the absence or presence of particles by an affinity based method or technique such as by Western blot, flow cytometry (e.g., FACS), or microscopy (e.g., fluorescent microscopy). In some embodiments, the binding agent allows for the enumeration or determining of the number and/or concentration of particles by an affinity based method or technique such as Western blot, flow cytometry (e.g., FACS), or microscopy (e.g., fluorescent microscopy).

In some embodiments, the methods provided herein involve determining the presence, absence, number, and/or concentration of particles in an output composition by particle (e.g., bead particle) counting by fluorescence activated cell sorting (FACS) using a flow cytometry device (e.g., Beckman Coulter Z2 Coulter Counter, Beckman Coulter Inc.). In some of the embodiments herein, FACS allows for detection of particles by detection of a material or molecule, such as a polysaccharide (e.g., dextran) or biomolecule present on the surface of the particles. In some embodiments, a FACs-based method comprises the step of preparing the output composition for detection by flow cytometry before the presence, absence, number and/or concentration of particles can be determined. For example, the output composition can be incubated with a fluorescently labeled binding agent that is specific for one or more markers present on the particle surface (e.g., dextran), and then the sample can be analyzed using a flow cytometer. In flow cytometry, cells and/or particles bound by fluorescently labeled affinity reagents are carried in a fluidic stream, are separated based on size and/or fluorescent signal and are subsequently analyzed and counted using a FACS software program (e.g., FlowJo software). The number or approximate number of particles can be determined by detection of the fluorescent signal, which optionally can be determined or processed by the FACS software program to provide the total or approximate number of particles in the output composition.

In some embodiments, non-affinity-based methods for determining or assessing particles in a sample can be employed. In some embodiments, the methods provided herein involve determining the presence, absence, number, and/or concentration of particles in an output composition by detection of particles using an automated cell counter (e.g., TC10 automated cell counter, Bio-Rad Laboratories Inc.). Such a method can further comprise the step of preparing the output composition for detection by an automated cell counter before the presence, absence, number and/or concentration of particles can be determined.

In some embodiments, the methods provided herein involve determining the presence, absence, number, and/or concentration of particles in an output composition by detection of particles using a hemocytometer (e.g., Hauser Nageotte Bright-Line™ Hemocytometer, Fischer Scientific), such as fitted to a microscope (e.g., Olympus IX70 inverted microscope). In some embodiments, such a method further comprises the step of preparing the output composition for detection before the presence, absence, number and/or concentration of particles can be determined. In some embodiments, particles present in a grid or region of a hemocytometer field can be visualized and/or counted, which, in some cases, can be performed manually. As an example, an exemplary hemocytometer is the Hauser Nageotte Bright-Line™ Hemocytometer, which contains approximately 40 rectangles and holds approximately a total of or about 50 μL liquid. Particles that are visualized in the 40 rectangles, including particles touching the rectangle lines, of the hemocytometer grid can be counted to obtain a particle count.

In some embodiments, counting can be repeated a plurality of times, such as two times, three times, four times, five times or more from an aliquot volume of the same sample (e.g. output composition) and the plurality of counts can be averaged and a standard deviation can be determined. In some embodiments, the number of particles per μL of the output composition can be calculated by dividing the averaged particle counts by the total volume of the sample added to the hemocytometer (e.g. 50 μL). In some embodiments, the average, standard deviation and coefficient of variation (100×(standard deviation/average)) of total particles (e.g., bead particles) per cell composition can be calculated from at least three replicate samples. In some embodiments, the number of particles per μL of the output composition can be calculated as described in Example 1.

In some embodiments, from the number or concentration of particles as determined in the output composition, the method further includes calculating the presence, absence, number, and/or concentration of particles in the cell composition from which the sample before lysis was derived or obtained. In some embodiments, to calculate the number of total particles (e.g., bead particles) in the cell composition from which the sample was derived or obtained, the concentration of particles (e.g. number of particles per μL as determined to be present in the output composition can be multiplied by the volume of the cell composition from which the sample was obtained or derived prior to performing the lysis methods.

III. Methods of Processing Cells in the Presence of Particles and Cell Compositions Containing Particles In some embodiments, the provided methods can be used for determining the presence, absence, number and/or concentration of particles (e.g., microspheres or bead particles) in a sample that is derived from or obtained from a cell composition. In some embodiments, the cell composition can be a pharmaceutical composition and/or formulated for administration to a subject. In some embodiments, the sample contains at least a portion of the cell composition. In some embodiments, the sample that is assessed for the presence, absence, number and/or concentration of particles includes or is a portion of the cell composition. In some embodiments, the sample represents no more than 0.1%, 0.25%, 0.5%, 0.75%, 1%, 1.5%, 2%, 2.5%, 5.0%, 10.0%, 20.0%, 30.0%, 40.0%, or 50.0% of the cell composition.

In some embodiments, the cell composition can be a cell preparation that has been processed in the presence of one or more particles (such as one or more microspheres or bead particles), such as for enrichment, separation, selection, isolation, stimulation, activation and/or expansion of one or more cells in a population of cells. In some embodiments, one or more particles (e.g., microspheres or bead particles) are mixed with cells, such as by incubating or contacting particles with a population of cells, thereby producing a cell composition. In some embodiments, the one or more particles are capable of binding one or more cells in the population. In some embodiments, the processing produces a cell composition that contains or potentially contains one or more cells specifically associated with one or more particles (e.g., microspheres or bead particles).

In some embodiments, the mixing, such as incubating or contacting, of the particles (e.g., microspheres or bead particles) with a population of cells facilitates or results in enrichment, separation, selection, isolation, activation, stimulation and/or expansion of cells in the population. In some embodiments, typically, the enrichment, separation, selection, isolation, activation, stimulation and/or expansion is achieved due to the presence of one or more biomolecules (e.g. protein, such as an antibody) present on the surface of the particles (e.g., microspheres or bead particles) that specifically interact with, such as bind or engage, one or more macromolecules (e.g., cell surface receptor) on the surface of one or more cells in the cell population. In some embodiments, presentation of the biomolecule on the particle can create a multivalent ligand in which several macromolecules on a cell or cells can bind or engage with a biomolecule present on the particle. In some embodiments, the processing produces a cell composition containing or potentially containing one or more cells specifically associated with one or more particles, for example, via the specific interaction between the biomolecule on the particle (e.g. microsphere or bead particle) and the macromolecule on the surface of the cell.

In some embodiments, the cell composition is derived from removal of one or more particles from an input composition. In some cases, the input composition is produced from mixing a population of cells with one or more particles. In some embodiments, the cell composition is produced by a method comprising mixing a population of cells with one or more particles to produce an input composition that is further processed by removing one or more of the particles from the cells.

In some embodiments, the cell composition is a cell preparation that has been processed in the presence of one or more particles and is further subjected to one or more steps for removal of the particles from the cell preparation. In some cases, the removal of particles is incomplete and the resulting cell composition contains residual particles. In some embodiments, a cell composition provided herein comprises or is suspected of comprising residual particles.

In some embodiments, the particle (e.g., bead particle) to cell ratio in a cell composition provided herein, such as for activation and/or expansion of a cell or a cell population, is about any of 1:1, 1:2, 1:3, 1:4, 1:5, 1:6, 1:7, 1:8, 1:9, 1:10, 1:12, 1:14; 1:16, 1:18, 1:20, 1:25, 1:30, 1:35, 1:40, 1:45, 1:50, 2:1, 2:2, 2:3, 2:4, 2:5, 2:6, 2:7, 2:8, 2:9, 2:10, 3:1, 3:2, 3:3, 3:4, 3:5, 3:6, 3:7, 3:8, 3:9, 3:10, 4:1, 4:2, 4:3, 4:4, 4:5, 4:6, 4:7, 4:8, 4:9, 4:10, 5:1, 5:2, 5:3, 5:4, 5:5, 5:6, 5:7, 5:8, 5:9, 5:10, 6:1, 6:2, 6:3, 6:4, 6:5, 6:6, 6:7, 6:8, 6:9, 6:10, 7:1, 7:2, 7:3, 7:4, 7:5, 7:6, 7:7, 7:8, 7:9, 7:10, 8:1, 8:2, 8:3, 8:4, 8:5, 8:6, 8:7, 8:8, 8:9, 8:10, 9:1, 9:2, 9:3, 9:4, 9:5, 9:6, 9:7, 9:8, 9:9, 9:10, 10:1, 10:2, 10:3, 10:4, 10:5, 10:6, 10:7, 10:8, 10:9, or 10:10. In some embodiments, the particle (e.g., bead particle) to cell ratio in a composition provided herein (e.g., for activation and/or expansion of a cell or a cell population) is about 1:1, about 1:2, about 1:10, about 4:1, or about 3:1.

In some embodiments, the cell composition comprises a plurality of particles with the same size (e.g., the same diameter). In some embodiments, the cell composition comprises a plurality of particles with at least two different sizes. For example, the cell composition may comprise one or more particles with a diameter of about 3 µm, one or more particles with a diameter of about 4 µm, one or more particles with a diameter of about 5 µm, one or more particles with a diameter of about 6 µm, one or more particles with a diameter of about 7 µm, one or more particles with a diameter of about 8 µm, one or more particles with a diameter of about 9 µm, one or more particles with a diameter of about 10 µm, one or more particles with a diameter of about 11 µm, one or more particles with a diameter of about 12 µm, one or more particles with a diameter of about 13 µm, one or more particles with a diameter of about 14 µm and/or one or more particles with a diameter of about 15 µm.

In some embodiments, the size of a cell in the cell composition is about 1.0 µm to about 30 µm, about 1.0 µm to about 25 µm, about 1.0 µm to about 20 µm, about 1.0 µm to about 15 µm, about 1.0 µm to about 10 µm, about 1.0 µm to about 5.0 µm, about 10 µm to about 15 µm, about 6 µm to about 12 µm, or about 7 µm to about 8 µm. In some embodiments, the size of the at least one cell is about at least or is at least 1 µm, 1.5 µm, 2.0 µm, 2.5 µm, 3.0 µm, 3.5 µm, 4.0 µm, 4.5 µm, 5.0 µm, 5.5 µm, 6.0 µm, 6.5 µm, 7.0 µm, 7.5 µm, 8.0 µm, 8.5 µm, 9.0 µm, 9.5 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, or 25 µm.

In some embodiments, a concentration of a cell composition or a sample obtained from or derived from the cell composition described herein is at least about $2 \times 10^5$ cells/mL, at least about $5 \times 10^5$ cells/mL, at least about $1 \times 10^6$ cells/mL, at least about $2.5 \times 10^6$ cells/mL, at least about $5 \times 10^6$ cells/mL, at least about $1 \times 10^7$ cells/mL, at least about $5 \times 10^7$ cells/mL, at least about $1 \times 10^8$ cells/mL, or at least about $5 \times 10^8$ cells/mL. In some embodiments, the volume of the cell composition or a sample obtained or derived from the cell composition described herein is from any of about 0.2 mL to 50 mL, 0.2 mL to 20 mL, 0.5 mL to 10 mL, 0.5 mL to 5 mL, or 0.75 mL to 1.5 mL. In some embodiments, the volume of the cell composition or a sample obtained or derived from the cell composition described herein is at least about or is at least 0.2 mL, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, about 1.8 mL, about 1.9 mL, about 2.0 mL, about 5.0 mL, about 10.0 mL, about 20 mL, or about 50 mL but no more than 100 mL.

A. Non-Cell Particles, e.g. Bead Particles

In some embodiments, the cells can be incubated or contacted with a particle, which typically is conjugated or linked to a biomolecule that is capable of specifically binding to a macromolecule on the surface of a cell. In some embodiments, the particle is or comprises a solid surface. In some embodiments, the particle is a bead particle.

In some embodiments, the particle can be a composite particle containing an inner core. In some embodiments, the inner core is a magnetic core, a paramagnetic core or a superparamagnetic core. In some embodiments, the inner core (e.g., magnetic core) is or contains any suitable metal. In some embodiments, the metal can be, but is not limited to, iron, nickel, copper, cobalt, gadolinium, manganese, tantalum, zinc, zirconium or any combinations thereof. Suitable substances that may be included in an inner core described herein (e.g., a magnetic core) includes, but is not limited to, metal oxides (e.g., iron oxides), ferrites (e.g., manganese ferrites, cobalt ferrites, nickel ferrites, etc.), hematite and metal alloys (e.g., CoTaZr). In some embodiments, the inner core comprises one or more of a ferrite, a metal, a metal alloy, an iron oxide, or chromium dioxide. In some embodiments, the inner core comprises elemental iron or a compound thereof. In some embodiments, the inner core comprises one or more of magnetite ($Fe_3O_4$), maghemite ($\gamma Fe_2O_3$), or greigite ($Fe_3S_4$). In some embodiments, the inner core comprises an iron oxide (e.g., $Fe_3O_4$). In some embodiments, the inner core comprises colloidal iron (e.g., colloidal iron oxide).

In some embodiments, the particle (e.g., bead particle) reacts in a magnetic field. In some embodiments, the particle is a magnetic particle (e.g., magnetic bead particle).

In some embodiments, the inner core can further contain a polymer (e.g., a biodegradable polymer), a polysaccharide, a silica, a fatty acid, a protein, a carbon or a combination thereof. In some embodiments, the polymer is one or more selected from the group consisting of: a polyethylene glycol, poly(lactic-co-glycolic acid), polyglutaraldehyde, polyurethane, polystyrene, and polyvinyl alcohol. In some embodiments, the polymer is polystyrene. In some embodiments, the polymer is polyglutaraldehyde. In some embodiments, the polymer is a biodegradable polymer. In some embodiments, the polysaccharide can be chitosan, agarose, starch, dextran, or a dextran derivative. In some embodiments, the polysaccharide is dextran or derivative thereof (e.g., amino dextran). In some embodiments, the silica is silicon oxide. In some embodiments, the protein is an albumin (e.g., human serum albumin). In some embodiments, the carbon is one or more selected from the group consisting of: an acrylamide and maleic acid. In some embodiments, the inner core comprises a metal oxide (e.g., an iron oxide) and a polysaccharide (e.g., dextran). In some embodiments, the inner core comprises colloidal iron (e.g., colloidal iron oxide) and a polysaccharide (e.g., dextran).

In some embodiments, the inner core comprises nanoparticles. In some embodiments, the inner core comprises microbeads (e.g., microbeads comprising dextran). Such nanoparticles or microbeads can each have their own inner core comprising a metal and/or polymer described herein and, optionally further comprise a coat such as a coat described herein. In some embodiments, an inner core described herein comprises nanoparticles and a polymer (e.g., silica). In some embodiments, an inner core described herein comprises microbeads and a polymer (e.g., silica).

In some the embodiments, an inner core described herein has a diameter of less than about 3000 nm, about 2000 nm, about 1000 nm, about 900 nm, about 800 nm, about 700 nm, about 600 nm, about 500 nm, about 400 nm, about 300 nm, about 200 nm, about 100 nm, about 90 nm, about 80 nm, about 70 nm, about 60 nm, about 50 nm, about 40 nm, about 30 nm, about 20 nm, or about 10 nm. In some the embodiments, the inner core has a diameter of about any of 3000 nm, about 2000 nm, about 1000 nm, about 900 nm, about 800 nm, about 700 nm, about 600 nm, about 500 nm, about 400 nm, about 300 nm, about 200 nm, about 100 nm, about 90 nm, about 80 nm, about 70 nm, about 60 nm, about 50 nm, about 40 nm, about 30 nm, about 20 nm, or about 10 nm. In some embodiments, the inner core has a diameter of about 100 nm or less. In some embodiments, the inner core has a diameter of about 50 nm or less.

In some of the embodiments, the particle can further contain one or more coat or coating such as one or more coat or coating on a surface of the particle (e.g., surface coating). In some embodiments, one or more coat or coating protects the inner core, provides a material for conjugation or coupling to a biomolecule and/or provides a biodegradable surface.

In some embodiments, a coat or coating (e.g., surface coating) described herein provides a protective coat. In some embodiments, the coat (e.g., protective coat) or coating (e.g., protective coating) protects, reduces or prevents oxidation of an inner core (e.g., magnetic core). For example, the coat may protect, reduce or prevent the magnetic core from oxidation. In some embodiments, the coat or coating retains an inner core to the particle (e.g., bead particle). In some embodiments, the coat or coating prevents deterioration of an inner core.

In some embodiments, the coat contains at least one material that can be coupled, linked or conjugated to a biomolecule. In some embodiments, the material can be coupled, linked or conjugated to one or more biomolecule such as a nucleic acid (e.g., DNA), protein, antibody, antigen, or any other biomolecule with an affinity (e.g., affinity reagent) for a desired target (e.g., T cells).

In some embodiments, the coat can contain a material that can include, but is not limited to, a polymer, a polysaccharide, a silica, a fatty acid, a protein, a carbon, or a combination thereof. In some embodiments, the polymer can be a polyethylene glycol, poly(lactic-co-glycolic acid), polyglutaraldehyde, polyurethane, polystyrene, or a polyvinyl alcohol. In some embodiments, the polymer is polyurethane. In some embodiments, the polymer is a biodegradable polymer. In some embodiments, the coat contains or includes a material that is or includes a polysaccharide that can be a chitosan, agarose, starch, dextran, and/or a dextran derivative. In some embodiments, the polysaccharide is dextran or derivative thereof (e.g., amino dextran). In some embodiments, the silica is silicon oxide. Methods of producing silicon oxide for coating an inner core are well known in the art. See U.S. Pat. No. 8,398,741. In some embodiments, the coat contains or includes a material that is or includes a protein that is an albumin (e.g., human serum albumin), Protein A, and Protein G. In some embodiments, the carbon is an acrylamide or maleic acid. In some embodiments, the material is coupled, linked or conjugated to a biomolecule described herein.

In some embodiments, a coat or coating described herein (e.g., a protective coat) has a thickness of less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, less than about 50 nm, or less than about 25 nm. In some embodiments, a coat or coating described herein (e.g., a protective coat) has a thickness of about 500 nm, about 450 nm, about 400 nm, about 350 nm, about 300 nm, about 250 nm, about 200 nm, about 150 nm, about 100 nm, about 75 nm, about 50 nm, or about 25 nm.

In some embodiments, a particle described herein (e.g., a bead particle) can have an inner core and a coat (e.g., protective coat) wherein the coat contains one or more material described herein. In some embodiments, a particle described herein (e.g., a bead particle) comprises a metal oxide core (e.g., an iron oxide inner core) and a coat (e.g., a protective coat), wherein the coat comprises at least one polysaccharide (e.g., amino dextran). In some embodiments, a particle described herein (e.g., a bead particle) comprises a metal oxide core (e.g., an iron oxide inner core) and a coat (e.g., a protective coat), wherein the coat comprises at least one polysaccharide (e.g., amino dextran) and at least one polymer (e.g., polyurethane). In some embodiments, a particle described herein (e.g., a bead particle) has a metal oxide core (e.g., an iron oxide inner core) and a coat (e.g., a protective coat), wherein the coat comprises at least one polysaccharide (e.g., amino dextran), at least one polymer (e.g., polyurethane) and silica. In some of any such embodiments herein, the metal oxide core is an iron oxide core comprising colloidal iron (e.g., colloidal iron oxide inner core). In some of any such embodiments herein, the metal oxide core comprises a polysaccharide (e.g., dextran) and colloidal iron. In some of any such embodiments, the coat has a thickness of about 400 nm.

In some of the embodiments herein, the particle (e.g., bead particle) has a diameter of greater than about 0.001 μm, greater than about 0.01 μm, greater than about 0.1 μm, greater than about 1.0 μm, greater than about 10 μm, greater than about 50 μm, greater than about 100 μm or greater than about 1000 μm and no more than about 1500 μm. In some embodiments, the particle (e.g., bead particle) has a diameter of about 1.0 μm to about 500 μm, about 1.0 μm to about 150 μm, about 1.0 μm to about 30 μm, about 1.0 μm to about 10 μm, about 1.0 μm to about 5.0 μm, about 2.0 μm to about 5.0 μm, or about 3.0 μm to about 5.0 μm. In some embodiments, the particle (e.g., bead particle) has a diameter of about 3 μm to about 5 μm. In some embodiments, the particle (e.g., bead particle) has a diameter of at least or at least about or about 0.001 μm, 0.01 μm, 0.1 μm, 0.5 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 12 μm, 14 μm, 16 μm, 18 μm or 20 μm.

In some embodiments, the particle (e.g., bead particle) has a diameter that is greater than about 1.5-fold, greater than about 2-fold, greater than about 3-fold, greater than about 4-fold, or greater than about 5-fold the diameter of the cell and no more than 10-fold the diameter of a cell in a cell composition or sample described herein. In some embodiments, the particle (e.g., bead particle) has a diameter that is less than 1.5-fold, less than 2-fold, less than 3-fold, less than 4-fold, or less than 5-fold the diameter of a cell in a cell composition or sample described herein. In some embodiments, the particle (e.g., bead particle) is substantially the same or about the same size as a cell in a cell composition or sample described herein such as within 1.5-fold the size of the cell (greater or less than no more than 1.5-fold the size of the cell).

In some embodiments, the particle (e.g., bead particle) can further contain one or more biomolecule, such as one or more biomolecule that is coupled, conjugated or linked (directly or indirectly) to the coat or coating of the particle. In some embodiments, biomolecules contemplated herein can include, but are not limited to, RNA, DNA, proteins (e.g., enzymes), antigens, polyclonal antibodies, monoclonal antibodies, antibody fragments, carbohydrates, lipids lectins, or any other biomolecule (e.g., streptavidin) with an affinity (e.g., affinity reagent) for a desired target. The one or more biomolecule may be attached directly or indirectly to the particle (e.g., bead particle) by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, a biomolecule (e.g., biotinylated anti-CD3 antibody) may be attached indirectly to the particle via another biomolecule (e.g., anti-biotin antibody) that is directly attached to the particle.

In some embodiments, the biomolecule is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). In some embodiments, the biomolecule is an antibody fragment (including antigen-binding fragment), e.g., a Fab, Fab'-SH, Fv, scFv, or (Fab')$_2$ fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species).

In some embodiments, the antibody is an anti-biotin antibody or an anti-IgG antibody. In some embodiments, the antibody or antigen-binding fragment thereof is biotinylated (e.g., biotinylated anti-CD3 antibody).

In some embodiments, the biomolecule specifically binds to a target. In some embodiments, the target is one or more macromolecule on the surface of a cell. Cells contemplated herein include, but are not limited to, T cells (e.g., CD4+ T cells, CD8+ T cells, etc.), B cells (e.g., memory B cells, plasma B cells, etc.), natural killer cells, eosinophils, mast cells, basophils, macrophages, and dendritic cells.

In some cases, a particle described herein (e.g., bead particle) provides a solid support or matrix to which a biomolecule, such as a biomolecule described herein (e.g., an antibody), can be bound, thereby facilitating separation, enrichment, selection, isolation, activation, stimulation and/or expansion of one more cell types in a cell population based on expression or expression level of one or more macromolecule on the surface of a cell, e.g. cell surface protein. Biomolecules that can be employed, include, but are not limited to RNA, DNA, proteins (e.g., enzymes), antigens, polyclonal antibodies, monoclonal antibodies, antibody fragments, carbohydrates, lipids lectins, or any other biomolecule (e.g., streptavidin) that is capable of specifically binding one or more macromolecule on the surface of a cell. In certain embodiments, the particle (e.g., a magnetic bead particle) comprises one or more biomolecule (e.g., an antibody) that binds directly or indirectly to one or more macromolecule on the surface of a cell.

In some embodiments, the particle comprises one or more biomolecule that directly interact with a macromolecule on the surface of a cell. In certain embodiments, the particle (e.g., a magnetic bead particle) interacts with a cell via one or more biomolecule (e.g., an antibody) specific for one or more macromolecules on the cell (e.g., one or more cell surface protein). In certain embodiments, the particle (e.g., a magnetic bead particle) is labeled with a first biomolecule described herein, such as a primary antibody (e.g., an anti-biotin antibody) or other first biomolecule, and then a second biomolecule, such as a secondary antibody (e.g., a biotinylated anti-CD3 antibody) or other second biomolecule (e.g., streptavidin), is added, whereby the secondary antibody or other second biomolecule specifically binds to such primary antibodies or other first biomolecule on the particle.

In some embodiments, the particle comprises a biomolecule that indirectly interacts with a macromolecule on the surface of a cell. In certain embodiments, the cell, rather than a particle described herein (e.g., a magnetic bead particle), is labeled with one or more biomolecule described herein. In certain embodiments, the cell is labeled with a first biomolecule described herein, such as a primary antibody (e.g., a biotinylated anti-CD3 antibody) or other first biomolecule (e.g., streptavidin), and then a particle carrying a second biomolecule, such as a secondary antibody (e.g., an anti-biotin antibody) or other second biomolecule, are added, whereby the secondary antibody or other second biomolecule specifically binds to such primary antibodies or other first biomolecule. In some embodiments, the one or more biomolecule is an antibody. In some embodiments, the one or more biomolecule is an anti-biotin antibody.

In some embodiments, a biomolecule (e.g. antibody) attached to a particle (e.g., bead particle) specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD1 1a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, a biomolecule (e.g. antibody) attached to a particle (e.g. bead particle) specifically binds to one or more of the following macromolecules on a cell (e.g. a T cell): CD28, CD62L, CCR7, CD27, CD127, CD3, CD4, CD8, CD45RA, and/or CD45RO.

In some embodiments, the biomolecule delivers a signal to a cell or acts as stimulating agent. For example, an antibody or antigen-binding fragment thereof (e.g., Fab) that is attached to a particle (e.g., bead particle) can provide an activation signal to a cell (e.g., a T cell) and induce cell activation and/or cell expansion. Such antibodies contemplated herein include, but are not limited to, an anti-CD2 antibody, an anti-CD3 antibody, an anti-CD28 antibody, an anti-CD137 antibody, an anti-CD134 antibody, or combinations thereof including antigen-binding fragments thereof. In some embodiments, such antibodies or antigen-binding fragments thereof are biotinylated (e.g., biotinylated anti-CD3 antibody).

In some embodiments, the one or more biomolecule is one or more antibody selected from the group consisting of: an anti-CD2 antibody, an anti-CD3 antibody, an anti-CD28 antibody, an anti-CD137 antibody, and an anti-CD134 antibody. In some embodiments, the one or more biomolecule is an anti-CD3 antibody and an anti-CD28 antibody. In some embodiments, the one or more biomolecule is an anti-CD2 antibody, an anti-CD3 antibody and an anti-CD28 antibody. In some embodiments, the one or more biomolecule is an anti-CD2 antibody, an anti-CD3 antibody, anti-CD28 antibody, and an anti-biotin antibody. In some embodiments, the one or more biomolecule is an anti-CD3 antibody, anti-CD28 antibody, and an anti-biotin antibody.

In some embodiments, the particle (e.g., bead particle) comprises a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments herein, the metal oxide core is a colloidal iron oxide core. In a further embodiment, the particle comprises one or more biomolecule that binds to a macromolecule (e.g., protein) on the surface of a cell, thereby causing association or binding of the particle to the cell in the cell composition or a sample of the cell composition. In some embodiments, the one or more biomolecule is selected from the group consisting of: RNA, DNA, proteins, antigens, polyclonal antibodies, monoclonal antibodies, carbohydrates, lipids or any other biomolecule (e.g., streptavidin) with an affinity (e.g., affinity reagent) for a desired target. In some embodiments, the biomolecule is an antibody or antigen-binding fragment thereof. In some embodiments, the particle comprises an anti-CD3 antibody and an anti-CD28 antibody. In some embodiments, the particle comprises an anti-CD2 antibody, an anti-CD3 antibody and an anti-CD28 antibody. In some embodiments, the particle comprises an anti-CD2 antibody, an anti-CD3 antibody, anti-CD28 antibody, and an anti-biotin antibody. In some embodiments, the particle comprises an anti-CD3 antibody, anti-CD28 antibody, and an anti-biotin antibody. In some embodiments, the particle comprises an anti-biotin antibody. In some embodiments, the bead particle has a diameter of about 3 µm to about 10 µm. In some embodiments, the bead particle has a diameter of about 3 µm to about 5 µm.

The particles (e.g., bead particles) used in the methods described herein can be produced or obtained commercially. Particles, including methods of producing particles, are well known in the art. See, for example, U.S. Pat. Nos. 6,074,884; 5,834,121; 5,395,688; 5,356,713; 5,318,797; 5,283,079; 5,232,782; 5,091,206; 4,774,265; 4,654,267; 4,554,088; 4,490,436; 4,452,773; U.S. Patent Application Publication No. 20100207051; and Sharpe, Pau T., Methods of Cell Separation, Elsevier, 1988. Commercially available particles (e.g., bead particles) include, but are not limited to, ProMag™ (PolySciences, Inc.); COMPEL™ (PolySciences, Inc.); BioMag® (PolySciences, Inc.), including BioMag® Plus (PolySciences, Inc.) and BioMag® Maxi (Bang Laboratories, Inc.); M-PVA (Cehmagen Biopolymer Technologie AG); SiMAG (Chemicell GmbH); beadMAG (Chemicell GmbH); MagaPhase® (Cortex Biochem); Dynabeads® (Invitrogen), including Dynabeads® M-280 Sheep Anti-rabbit IgG (Invitrogen), Dynabeads® FlowComp™ (e.g., Dynabeads® FlowComp™ Human CD3, Invitrogen), Dynabeads® M-450 (e.g., Dynabeads® M-450 Tosylactivated, Invitrogen), Dynabeads® Untouched™ (e.g., Dynabeads® Untouched™ Human CD8 T Cells, Invitrogen), and Dynabeads® that bind, expand and/or activate T cells (e.g., Dynabeads® Human T-Activator CD3/CD28 for T Cell Expansion and Activation, Invitrogen); Estapor® M (Merk Chimie SAS); Estapor® EM (Merk Chimie SAS); MACSiBeads™ Particles (e.g., anti-biotin MACSiBead Particles, Miltenyi Biotec, catalog #130-091-147); Streptamer® Magnetic Beads (IBA BioTAGnology); Strep-Tactin® Magnetic Beads (IBA BioTAGnology); Sicastar®-M (Micormod Partikeltechnologie GmbH) Micromer®-M (Micromod Partikeltechnologie); MagneSil™ (Promega GmbH); MGP (Roche Applied Science Inc.); Pierce™ Protein G Magnetic Beads (Thermo Fisher Scientific Inc.); Pierce™ Protein A Magnetic Beads (Thermo Fisher Scientific Inc.); Pierce™ Protein A/G Magnetic Beads (Thermo Fisher Scientific Inc.); Pierce™ NHS-Activated Magnetic Beads (Thermo Fisher Scientific Inc.); Pierce™ Protein L Magnetic Beads (Thermo Fisher Scientific Inc.); Pierce™ Anti-HA Magnetic Beads (Thermo Fisher Scientific Inc.); Pierce™ Anti-c-Myc Magnetic Beads (Thermo Fisher Scientific Inc.); Pierce™ Glutathione Magnetic Beads (Thermo Fisher Scientific Inc.); Pierce™ Streptavidin Magnetic Beads (Thermo Fisher Scientific Inc.); MagnaBind™ Magnetic Beads (Thermo Fisher Scientific Inc.); Sera-Mag™ Magnetic Beads (Thermo Fisher Scientific Inc.); Anti-FLAG® M2 Magnetic Beads (Sigma-Aldrich); SPHERO™ Magnetic Particles (Spherotech Inc.); and HisPur™ Ni-NTA Magnetic Beads (Thermo Fisher Scientific Inc.).

B. Cells and Processing of Cells in the Presence of Particles

In some embodiments, the cells in a cell composition or processed for the preparation of a cell composition described herein generally are eukaryotic cells, such as mammalian cells, and typically are human cells. In some embodiments, the cells are or include cells of the immune system, such as cells of the innate or adaptive immunity, e.g., myeloid or lymphoid cells, including lymphocytes, typically T cells and/or NK cells. In some embodiments, the cell of the immune system (e.g., immune cell) is a T cell, B cell, macrophage, neutrophil, natural killer (NK) cell or dendritic cell. In some embodiments, cell composition comprises one or more cells of the immune system, such as CD4+ or CD8+ T cells. In some embodiments, the cell is or the cell composition comprises monocytes or granulocytes, e.g., myeloid cells, macrophages, neutrophils, dendritic cells, mast cells, eosinophils, and/or basophils. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells are primary cells, e.g., primary human cells.

In some embodiments, the cells in the cell composition are obtained from a biological sample. A biological sample includes a tissue sample, a fluid sample, and other biological sample taken directly from a subject, as well as a biological sample resulting from one or more processing steps, such as separation, centrifugation, genetic engineering (e.g., transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom. In some aspects, the biological sample from which the cells are derived, obtained or isolated is blood or a blood-derived sample, or is derived from an apheresis or leukapheresis product. In some embodiments, the cells from the circulating blood of a subject is obtained, e.g., by apheresis or leukapheresis. In some embodiments, the cells are immune cells (e.g., myeloid or lymphoid cells, including lymphocytes, typically T cells and/or NK cells) obtained or derived from the blood, bone marrow, lymph, or lymphoid organs. Exemplary biological samples also include, but are not limited to, whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. In some embodiments, the biological sample, contains lymphocytes, including T cells, monocytes, granulocytes, B cells, other nucleated white blood cells, red blood cells, and/or platelets, and in some aspects contains cells other than red blood cells and platelets.

In some embodiments, cells in a blood sample collected from a subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished with a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++ free PBS. In certain embodiments, components of a blood sample are removed and the cells are directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the cells are derived from cell lines, e.g., T cell lines. The cells in some embodiments are obtained from a xenogeneic source, for example, from mouse, rat, non-human primate, and pig.

In some embodiments, the cells in the cell composition are or include cells for use in the context of cell therapy, e.g. adoptive cell therapy. In some cases, the biological sample is from an autologous source. In some cases, the biological sample is from an allogeneic source. In some embodiments, the methods described herein include isolating cells from a subject, preparing, processing, culturing, and/or engineering the cells, and re-introducing the cells into the same subject, before or after cryopreservation.

In some embodiments, the cells in the cell composition are or include cells obtained from a biological sample that has undergone one or more preparation and/or non-affinity based cell separation steps. In some examples, the cells or the cell population has been washed, centrifuged and/or incubated in the presence of one or more reagents, for example, to remove unwanted components, enrich for desired components, lyse or remove cells sensitive to particular reagents. In some examples, the cells or the cell population is prepared or obtained based on one or more property, such as density, adherent properties, size, sensitivity and/or resistance to particular components.

In some embodiments, a particle (e.g., bead particle) comprising a biomolecule described herein can be used in affinity- or immunoaffinity-based separation methods, such as during processing of a cell composition. Typically, the biomolecule, such as an antibody, is specific for one or more macromolecule (e.g., cell surface receptor) that is expressed or present on the surface of a cell. In some embodiments, the cell composition comprises one or more cells (e.g., 1, 2, 3, 4 or more cells) of the same cell type. In some embodiments, the cell composition comprises one or more cells (e.g., 1, 2, 3, 4 or more cells) of different cell types. The particle generally is directly or indirectly attached to the biomolecule, e.g., an antibody. In some embodiments, any known method for separation using such particles (e.g., bead particle) may be used. For example, the isolation in some aspects includes separation of cells in a cell population by incubation with at least one particle carrying on its surface a biomolecule, e.g. an antibody, that specifically binds to one or more macromolecule on a cell, followed generally by washing steps and separation of cells having bound the biomolecule (e.g., antibody) from those cells having not bound to the biomolecule (e.g., antibody).

In some embodiments, such separation steps in a separation method can be based on enrichment for a particular cell population by positive selection, in which the cells having bound the reagents are retained for further use. In some aspects, multiple rounds of separation steps are carried out in which one or more positive selections can be performed. In some cases, multiple cell types can simultaneously be positively selected by incubating the cells with a plurality of biomolecules such as antibodies that bind to one or more macromolecule expressed on the various cell types.

In some embodiments, the separation method can also employ one or more negative selection step, in which cells having not bound to the biomolecule are the enriched cell population. In some aspects, one or more positive selection step is combined with one or more negative selection step, for example, where the positive and/or negative fractions are retained and further processed or subject to further separation positive and/or negative fraction steps. For example, the positively or negatively selected fraction from one step can be subjected to another separation step, such as a subsequent positive or negative selection. In some aspects, negative selection can be particularly useful where no biomolecule (e.g., antibody) is available that specifically identifies a cell type in a heterogeneous population, such that separation is best carried out based on markers (e.g., macromolecules) expressed by cells other than the desired population. Generally, such methods employ at least one positive selection step, whereby the particles (e.g., a particle comprising a biomolecule) may remain associated with the cell.

It is within the level of a skilled artisan to determine the particular particle (e.g., a particle comprising a biomolecule) to employ for enriching or separating a particular cell type or subset of cells from a population. For example, the particular choice of a biomolecule attached to a particle (e.g., bead particle) will depend on the particular cell type or subset of cells to be separated or enriched, the availability of biomolecules against a particular cell type or subset of cells, the choice of one or more positive selection or a combination of positive and negative selection methods and other factors within the level of a skilled artisan.

In an exemplary aspect, specific subpopulations of T cells can be isolated by positive and/or negative selection techniques, for example, for cells positive or expressing high levels of one or more surface markers (e.g., one or more macromolecules), such as CD28+, CD62L+, CCR7+, CD27+, CD127+, CD3+, CD4+, CD8+, CD45RA+, and/or CD45RO+ T cells. In some aspects, such enrichment and separation methods can be used to obtain a T cell population suitable for processing, preparing and/or engineering cells for adoptive cell therapy methods.

In some embodiments, T cells are separated from a PBMC sample by negative selection of markers expressed on non-T cells, such as B cells, monocytes, or other white blood cells, such as NK cells. In some aspects, a CD4+ or CD8+ positive selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood.1:72-82;

Wang et al. (2012) J Immunother. 35(9):689-701. In some embodiments, combining $T_{CM}$-enriched CD8+ T cells and CD4+ T cells further enhances efficacy.

In embodiments, memory T cells are present in both CD62L+ and CD62L− subsets of CD8+ peripheral blood lymphocytes. A PBMC sample can be enriched for or depleted of CD62L−CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order. In some cases, the combination of positive and negative selection can be used to sort CD4+ T helper cells into naïve, central memory, and effector cells by identifying cell populations that have cell surface antigens. In some embodiments, naive CD4+ T lymphocytes are CD45RO−, CD45RA+, CD62L+, and CD4+ T cells. In some embodiments, central memory CD4+ cells are CD62L+ and CD45RO+. In some embodiments, effector CD4+ cells are CD62L− and CD45RO−.

In some embodiments, the cells and/or cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.). Immunomagnetic methods of cell separation can utilize a paramagnetic bead particle comprising a magnetic core (e.g., iron oxide core), such as any described above (e.g., such as Dynabeads® or MACSiBeads™ Particles). In some embodiments, the magnetic bead particle comprises a magnetically responsive material bound to a specific biomolecule, such as an antibody or other biomolecule. There are many well-known magnetically responsive materials used in magnetic separation methods. Suitable magnetic bead particles include those described in herein as well as in Molday, U.S. Pat. No. 4,452,773 and in European Patent Specification EP 452342 B. Colloidal sized particles, such as those described in Owen U.S. Pat. No. 4,795,698, and Liberti et al., U.S. Pat. No. 5,200,084 are other examples of suitable magnetic bead particles.

In some aspects, a cell composition or a sample obtained or derived from a cell composition described herein to be separated is incubated with at least one magnetic bead particle described herein. The incubation generally is carried out under conditions whereby biomolecules, e.g., antibodies, which are attached to the magnetic bead particle, specifically bind to cell surface macromolecules if present on cells within the sample or cell composition. In some aspects, the sample or cell composition is placed in a magnetic field, and those cells having magnetically responsive or magnetizable bead particles attached thereto will be attracted to the magnet and separated from cells not having such bead particles attached thereto.

In some embodiments, the affinity-based selection is via magnetic-activated cell sorting (MACS) (Miltenyi Biotech, Auburn, Calif.). MACS systems are capable of high-purity selection of cells having magnetic bead particles attached thereto. In certain embodiments, MACS operates in a mode wherein the non-target cells and target cells are sequentially eluted after the application of the external magnetic field. That is, cells attached to magnetic bead particles (e.g., target cells) are held in place while the unattached cells (e.g., non-target cells) are eluted. Then, after this first elution step is completed, the target cells that were trapped in the magnetic field and were prevented from being eluted are freed in some manner such that they can be eluted and recovered. In certain embodiments, the non-target cells are labelled and depleted from the heterogeneous population of cells.

For positive selection, cells that are attracted to the magnet are retained; for negative selection, cells that are not attracted to the magnet (unlabeled cells) are retained.

In certain embodiments, the isolation or separation is carried out in an integrated or self-contained system, device, or apparatus, for example, to provide a closed or sterile environment, for example, to minimize error, user handling and/or contamination. In some cases, one or more other further processing steps also can be carried out in the system, such as one or more other processing, incubation, culture, and/or formulation steps. In one example, the system is a system as described in International Patent Application, Publication Number WO2009/072003, or US 20110003380. In some embodiments, the isolation or separation is carried out in an automated or programmable fashion. In some aspects, the system or apparatus includes a computer and/or computer program in communication with the system or apparatus, which allows a user to program, control, assess the outcome of, and/or adjust various aspects of the isolation or separation or one or more other steps of the process.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetic bead particles that are supplied in a sterile, non-pyrogenic solution. In some embodiments, after labelling of cells with magnetic bead particles the cells are washed to remove excess magnetic bead particles. A cell preparation bag is then connected to the tubing set, which in turn is connected to a bag containing buffer and a cell collection bag. The tubing set consists of pre-assembled sterile tubing, including a pre-column and a separation column, and are for single use only. In some embodiments, the tubing set does not comprise a pre-column. After initiation of the separation program, the system automatically applies the cell sample onto the separation column. Labelled cells are retained within the column, while unlabeled cells are removed by a series of washing steps. In some embodiments, the cell populations for use with the methods described herein are labeled with magnetic bead particles, such as those described herein, and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unit that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood.1:72-82, and Wang et al. (2012) J Immunother. 35(9):689-701.

In some embodiments, a particle comprising a biomolecule can be used connection with stimulation, activation and/or expansion of one or more cell types. In some embodiments, the biomolecule provides a stimulating agent that induces the proliferation, expansion, activation and/or survival of cells in the cell population, for example, to mimic antigen exposure and/or to induce cell signaling through one or more cell surface receptors In some embodiment, the biomolecule, e.g. an antibody or ligand, coated or bound to a particle described herein, provides a stimulating condition capable of activating an intracellular signaling domain of a TCR complex. In some aspects, the biomolecule turns on or initiates TCR/CD3 intracellular signaling cascade in a T cell. In some embodiments, signaling can be potentiated or enhanced in the presence of a costimulatory signal. In some embodiments, biomolecules that can promote stimulation or activation can include antibodies, such as those specific for a TCR component and/or costimulatory receptor, e.g., anti-CD3, anti-CD28, for example. In some embodiments, when an anti-CD3 antibody is immobilized on a surface, such as a particle (e.g. microsphere or bead particle), it can deliver an activating and proliferation-inducing signal by crosslinking of the T cell receptor complex on the surface of T cells. In some cases, by immobilizing anti-CD3 and anti-CD28 to simultaneously deliver a signal and a costimulatory signal, proliferation can be increased. Various solid phase surface particles, including microsphere and bead particles, are known that are immobilized with anti-CD3 and anti-CD28 beads (WO09429436; EP01257632; US2008/0317724 and U.S. Pat. No. 8,012,750). In some cases, the particles can include nanoparticles or microparticles.

Typically, it has been shown that stimulation or activation with anti-CD3/anti-CD28 particles is generally greater when effected using microparticles as compared to nanoparticles. For example, it has been shown that micron-sized particles, which are close in size to T cells, provide for optimal T cell stimulation (see e.g. Steenbloc and Fahmy, (2008) Molecular Therapy, 16:765-772; Mescher et al. (1992) J. Immunol., 149:2402-2405). A problem with existing methods for assessing the presence of particles is that many cannot differentiate between particles that are substantially the same size as a cell. In some embodiments, the provided methods overcome these problems, since the cells are lysed while leaving the particles (e.g. bead particles) intact. In some embodiments, anti-CD3/anti-CD28 microparticles (e.g. bead particles) have a size from or from about 1 µm to 24 µm, such as 2 µm to 10 µm or 3 µm to 5 µm, such as about or at least about or 3 µm, 3.5 µm, 4.0 µm, 4.5 µm or 5.0 µm.

Optionally, the stimulation, activation or expansion can also include the addition of one or more other stimulating conditions, such as to a culture medium. In some embodiments, stimulation conditions include addition of a stimulating cytokine, for example, IL-2 and/or IL-15, for example, at an IL-2 concentration of at least about 10 units/mL. In some embodiments, the conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,1 77 to Riddell et al., Klebanoff et al.(2012) J Immunother. 35(9): 651-660, Terakura et al. (2012) Blood.1:72-82, and/or Wang et al. (2012) J Immunother. 35(9):689-701.

In such aspects, one or more particles (e.g. bead particles) may be retained with one or more of the cells. In some embodiments, the particles (e.g. bead particles, including magnetizable particles) are left attached to the cells that are to be subsequently incubated, cultured and/or engineered; in some aspects, the particles are left attached to the cells for administration to a patient.

In some embodiments, the particles (e.g. bead particles, including magnetizable or magnetically responsive particles) are removed from the cell composition. In some embodiments, the particles (e.g. bead particles, including magnetizable or magnetically responsive particles) are not completely removed from the cell composition, thereby producing a residual bead cell composition. Methods for removing particles (e.g. bead particles or magnetizable particles) from cells are known. In come embodiments, the use of competing non-labeled antibodies can be used, which, for example, bind to the primary antibody and alter its affinity for its antigen on the cell, thereby permitting for gentle detachment. In some cases, after detachment, the competing antibodies may remain associated with the particle (e.g. bead particle) while the unreacted antibody is or may be washed away and the cell is free of isolating, selecting, enriching and/or activating antibody. Exemplary of such a reagent is DETACaBEAD (Friedl et al. 1995;

Entschladen et al. 1997). In some embodiments, particles (e.g. bead particles) can be removed in the presence of a cleavable linker (e.g. DNA linker), whereby the particle-bound antibodies are conjugated to the linker (e.g. CELLection, Dynal). In some cases, the linker region provides a cleavable site to remove the particles (e.g. bead particles) from the cells after isolation, for example, by the addition of DNase or other releasing buffer. In some embodiments, other enzymatic methods can also be employed for release of a particle (e.g. bead particle) from cells. In some embodiments, the particles (e.g. bead particles or magnetizable particles) are biodegradable.

In some embodiments, the preparation methods include steps for freezing, e.g., cryopreserving, the cells or cell population in the cell composition, either before or after isolation, incubation, and/or engineering. In some embodiments, the freeze and subsequent thaw step removes granulocytes and, to some extent, monocytes in the cell composition. In some embodiments, the cells or cell population in the cell composition is suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

C. Pharmaceutical Compositions and Formulations

In some embodiments, the cell composition is a pharmaceutical composition or formulation that includes a therapeutically effective amount of cells for administration. In some embodiments, the pharmaceutical composition or formulation can be a unit dose form composition including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation or composition would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the pharmaceutical compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The pharmaceutical compositions can include aqueous solutions.

The formulation or composition can be used either alone or in combination with other agents in a therapy. For instance, the composition may be co-administered with at least one additional therapeutic agent. In some embodiments, the formulation or composition may contain more than one active ingredient (e.g., therapeutic agent) useful for the particular indication, disease, or condition being treated with the cells, preferably those with activities complementary to the cells, where the respective activities do not adversely affect one another. Such active ingredients (e.g., therapeutic agents) are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. In some embodiments, the composition of the invention is in a separate formulation from the additional therapeutic agent. In some embodiments, the administration of the composition of the invention can occur prior to, simultaneously, and/or following administration of the additional therapeutic agent.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells. In some embodiments, the cells are formulated for administration in a single pharmaceutical composition, such as in single dosage form.

In some embodiments, the cells are formulated for administration in multiple dosage form. In some cases, such as in the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, such as generally no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period. Thus, in some aspects, the cells are administered in a single pharmaceutical composition. In some embodiments, the cells are administered in a plurality of compositions, collectively containing the cells of a single dose.

In some embodiments, the cells are formulated for administration in the range from about $10^5$ to about $10^6$ of such cells per kilogram body weight of the subject, and/or a number of such cells that is no more than about $10^5$ or about $10^6$ such cells per kilogram body weight of the subject. For example, in some embodiments, the cells are formulated for administration of a dose that includes less than or no more than at or about $1\times10^5$, at or about $2\times10^5$, at or about $5\times10^5$, or at or about $1\times10^6$ of such cells per kilogram body weight of the subject. In some embodiments, the cells are formulated for administration of a dose that includes at or about $1\times10^5$, at or about $2\times10^5$, at or about $5\times10^5$, or at or about $1\times10^6$ of such cells per kilogram body weight of the subject, or a value within the range between any two of the foregoing values. In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some embodiments, the cells are formulated in the composition in an amount to provide one or more unit doses of cells, which may be an amount or number of the cells to be administered to the subject in a single dose or in one or more split doses. In some embodiments, the unit dose includes less than about $1\times10^8$, less than about $5\times10^7$, less than about $1\times10^6$ or less than about $5\times10^5$ of the engineered cells, of total cells, of T cells, or PBMCs, per kg of the subject to be treated and/or from which the cells have been derived. In some embodiments, each unit dose contains at least or about at least or about or $2\times10^6$, $5\times10^6$, $1\times10^7$, $5\times10^7$, or $1\times10^8$ engineered cells, total cells, T cells, or PBMCs.

In some embodiments, the cells and compositions are formulated for administration using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

IV. Articles of Manufacture and Kits

Also provided are articles of manufacture or kits containing the reagents or components for performing the provided method. The articles of manufacture include one or more containers, typically a plurality of containers, packaging material, and a label or package insert on or associated with the container or containers and/or packaging, generally including instructions for performing the provided method.

In some embodiments, the articles of manufacture include one or more lysis solution (e.g., hypertonic solutions and/or hypotonic solutions) for performing the method, which are packaged as articles of manufacture containing packaging materials and, optionally, instructions for performing the method. In some embodiments, the articles of manufacture and kits may further contain reagents and/or instruments for enumerating or detecting the presence or absence of particles in a cell composition. Reagents include, but are not limited to, an affinity or detection reagent for detecting a biomolecule on the surface of a particle (e.g. anti-dextran antibody), rinse or wash buffer or solution, which each, optionally, can be contained in a packaging material. In some embodiments, the articles of manufacture include one or more instruments for performing the method. Instruments include, but are not limited to, a counting apparatus (e.g., hemocytometer), magnets, and pipette (e.g., automatic pipette).

In some embodiments, the articles of manufacture also can include one or more reagents for detection, selection, enrichment, isolation, activation and/or stimulation of cells. In some embodiments, such reagents can include particles (e.g. bead particles) that specifically bind to a macromolecule on the surface of a cell to effect one or more of detection, selection, enrichment, isolation, activation and/or stimulation of cells. In some embodiments, the particles are conjugated with an anti-CD3 and/or anti-CD28 antibody. In some embodiments, the particles can include any as described herein or known in the art.

Examples of packaging materials can include, for example, bottles, tubes, bags, vials, containers, syringes, bottles or any packaging material suitable for carrying or holding the lysis solution or solutions. In general, the packaging is one that is non-reactive with the lysis solution or buffer. The containers may be formed from a variety of materials such as glass or plastic. In some embodiments, the container has a sterile access port.

The article of manufacture or kit may further include a package insert with instructions for enumerating or detecting the presence or absence of non-cell particles in a cell composition. The label or a package insert, which is on or associated with the container, may indicate directions for reconstitution and/or use of the reagents, lysis solutions, materials and/or instruments in accord with the present disclosure. The label or package insert may further indicate that the lysis solutions, reagents and/or materials are useful for enumerating or detecting the presence of absence of non-cell particles in a cell composition for use in therapy (e.g., adoptive cell therapy), such as in accord with the present disclosure.

V. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein, including below, for clarity and/or for ready reference, and the inclusion of such definitions herein should not necessarily be construed to represent a substantial difference over what is generally understood in the art.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. In some embodiments, "about" refers to a range of ±50%, ±40%, ±30%, ±25%, ±20%, ±15%, ±10%, ±5%, or ±1% of the value or parameter.

As used herein, the singular forms "a," "an," and "the" include plural referents unless the context clearly dictates otherwise. For example, "a" or "an" means "at least one" or "one or more." It is understood that aspects, embodiments, and variations described herein include "comprising," "consisting," and/or "consisting essentially of" aspects, embodiments and variations.

As used herein, a "cell composition" refers to any mixture of two or more products, including cells. Such composition can, in some cases, also include non-cell particles (e.g. bead particles). It may be a solution, a suspension, liquid, powder, a paste, aqueous, non-aqueous or any combination thereof.

The term "package insert" is used to refer to instructions customarily included in commercial packages of therapeutic products, that contain information about the indications, usage, dosage, administration, combination therapy, contraindications and/or warnings concerning the use of such therapeutic products.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VI. Exemplary Embodiments

Among the embodiments provided herein are:

1. A method for enumerating or detecting the presence or absence of particles in a cell composition, the method comprising the steps of:

a) performing one or more incubations, thereby producing an output composition, wherein the one or more incubations comprise incubating a sample comprising at least a portion of a cell composition or a sample derived from the cell composition under a condition sufficient to induce osmotic lysis of one or more cells in the sample; and b) determining the presence, absence, number and/or concentration of particles in the output composition, thereby enumerating or detecting the presence or absence of particles in the cell composition.

2. The method of embodiment 1, wherein the condition sufficient to induce osmotic lysis comprises contacting the sample with a hypotonic solution.

3. The method of embodiment 1 or embodiment 2, wherein the incubating under a condition to induce osmotic lysis produces a lysed cell composition and the one or more incubations in step a) further comprises incubating the lysed cell composition or a composition derived from the lysed cell composition with a hypertonic solution.

4. A method for enumerating or detecting the presence or absence of particles in a cell composition, the method comprising the steps of:
   a) performing one or more incubations, thereby producing an output composition, wherein the one or more incubations in step a) comprises:
      i) incubating a sample comprising at least a portion of a cell composition or a sample derived from the cell composition with a hypotonic solution or a hypertonic solution under a condition sufficient to induce lysis of one or more cells in the sample, thereby producing a lysed cell composition, and
      ii) incubating at least a portion of the lysed cell composition or a sample derived from the lysed cell composition with the other of the hypotonic solution or the hypertonic solution; and
   b) determining the presence, absence, number and/or concentration of particles in the output composition, thereby enumerating or detecting the presence or absence of particles in the cell composition.

5. A method of enumerating or detecting the presence or absence of particles in a cell composition, the method comprising the steps of:
   a) performing one or more incubations, thereby producing an output composition, wherein the one or more incubations in step a) comprises
      i) incubating a sample comprising at least a portion of a cell composition or a sample derived from the cell composition with a hypotonic solution under a condition sufficient to induce lysis of one or more cells in the sample, thereby producing a lysed cell composition, and
      ii) incubating at least a portion of the lysed cell composition or a sample derived from the lysed cell composition with a hypertonic solution; and
   b) determining the presence, absence, number and/or concentration of particles in the output composition, thereby enumerating or detecting the presence or absence of particles in the cell composition.

6. The method of any one of embodiments 1-5, wherein:
   the cell composition comprises or is suspected of comprising one or more of the particles bound to the surface of one or more cells in the cell composition;
   the cell composition comprises or is suspected of comprising residual particles;
   the cell composition is derived from a composition containing cells bound to one or more of the particles; and/or
   the cell composition is derived from removal of particles from an input composition.

7. The method of any one of embodiments 1-6, wherein the cell composition is produced by a method comprising:
   (1) mixing a population of cells with one or more of the particles thereby generating an input composition; and
   (2) removing one or more of the particles from the cells in the input composition, thereby producing the cell composition.

8. The method of embodiment 7, wherein the one or more of the particles are capable of binding one or more cells in the population.

9. The method of any one of embodiments 1-8, wherein the particles are bead particles.

10. The method of any one of embodiments 1-9, wherein the one or more incubations in step a) reduces or removes cell debris from the output composition.

11. The method of any one of embodiments 1-10, wherein step a) further comprises rinsing or washing the output composition.

12. The method of embodiment 11, wherein rinsing or washing the output composition comprises pelleting the particles and removing a volume or reducing a volume of the output composition.

13. The method of embodiment 12, comprising reducing the volume of the output composition to about the same volume of the sample prior to the one or more incubations of step a).

14. The method of embodiment 12, comprising reducing the volume of the output composition by less than 100% but greater than or greater than about 50%, 60%, 70%, 80%, 90% or 95%.

15. The method of any one of embodiments 1-14, wherein one or more of the particles comprises a biomolecule capable of binding to a macromolecule on a surface of a cell in the cell composition.

16. The method of embodiment 15, wherein the biomolecule is an antibody or antigen-binding fragment thereof.

17. The method of any one of embodiments 2-16, wherein the hypotonic solution has an osmolarity less than 270 mOsm/L.

18. The method of any one of embodiments 2-17, wherein:
   the hypotonic solution has an osmolarity between or between about 0 mOsm/L and 270 mOsm/L, 50 mOsm/L and 200 mOsm/L or 10 mOsm/L and 100 mOsm/L; or
   the hypotonic solution has an osmolarity less than or less than about 250 mOsm/L, 200 mOsm/L, 150 mOsm/L, 100 mOsm/L, 50 mOsm/L, 10 mOsm/L or less.

19. The method of any one of embodiments 2-18, wherein:
   the hypotonic solution comprises a solute concentration of between or between about 0 mM and 140 mM; or
   the hypotonic solution comprises a solute concentration of less than or about less than 140 mM, less than or about less than 100 mM, less than or about less than 50 mM or less than or about less than 10 mM.

20. The method of any one of embodiments 2-19, wherein:
   the hypotonic solution comprises a percentage weight for volume (% w/v) of solute of between or between about 0% and 0.8% or 0% and 0.5%; or
   the hypotonic solution comprises a % w/v of solute of less than or about less than 0.8%, less than or about less than 0.6%, less than or about less than 0.4% or less than or about less than 0.2%.

21. The method of any one of embodiments 2-20, wherein the hypotonic solution is solute-free.

22. The method of any one of embodiments 2-21, wherein the hypotonic solution is sterile water for injection.

23. The method of any one of embodiments 3-22, wherein the hypertonic solution has an osmolarity greater than 300 mOsm/L.

24. The method of any one of embodiments 3-23, wherein:
the hypertonic solution has an osmolarity of greater than or about 300 mOsm/L, greater than or about 400 mOsm/L, greater than or about 800 mOsm/L, greater than or about 1200 mOsm/L, greater than or about 1500 mOsm/L, greater than or about 2000 mOsm/L, greater than or about 2500 mOsm/L, greater than or about 3000 mOsm/L or greater than or about 4000 mOsm/L; or
the hypertonic solution has an osmolarity of between or about between 300 mOsm/L and 5000 mOsm/L, 1000 and 5000 mOsm/L or 1000 and 3000 mOsm/L.

25. The method of any one of embodiments 3-24, wherein:
the hypertonic solution has a solute concentration of greater than or about 200 mM, greater than or greater than about 400 mM, greater than or greater than about 600 mM, greater than or greater than about 800 mM, greater than or greater than about 1000 mM greater than or greater than about 2000 mM; or greater than or greater than about 5000 mM; or
the hypertonic solution has a solute concentration of between or between about 200 mM and 5000 mM, 500 mM and 2000 mM or 1000 mM and 2000 mM.

26. The method of any one of embodiments 3-25, wherein:
the hypertonic solution comprises a percentage weight for volume (% w/v) of solute of between or between about 1.5% and 15% or 2.5% and 12%; or
the hypertonic solution comprises a % w/v of solute of greater than or about greater than 1.5%, greater than or about greater than 3.0%, greater than or about greater than 6.0% or greater than or about greater than 8.0% or greater than or about greater than 10.0%.

27. The method of any one of embodiments 3-26, wherein the hypertonic solution comprises a solute that is NaCl.

28. The method of any one of embodiments 1-27, wherein the concentration of the cell composition is at least or at least about $2 \times 10^5$ cells/mL, at least or at least about $5 \times 10^5$ cells/mL, at least or at least about $1 \times 10^6$ cells/mL, at least or at least about $5 \times 10^6$ cells/mL, or at least or at least about $1 \times 10^7$ cells/mL.

29. The method of any one of embodiments 1-28, wherein:
the volume of the cell composition is from or from about 0.2 mL to 50 mL, 0.2 mL to 20 mL, 0.5 mL to 10 mL, 0.5 mL to 5 mL, or 0.75 mL to 1.5 mL; or
the volume of the cell composition is at least or at least about 0.2 mL, 0.5 mL, 1.0 mL, 2.0 mL, 5.0 mL, 10.0 mL or 20 mL, 50 mL or more.

30. The method of any one of embodiments 1-29, wherein one or more of the particles have or comprise particles having a diameter of greater than 0.001 µm, greater than 0.01 µm, greater than 0.1 µm, greater than 1.0 µm, greater than 10 µm, greater than 50 µm, greater than 100 µm or greater than 1000 µm.

31. The method of any one of embodiments 1-30, wherein one or more of the particles have or comprise particles having a diameter of 1.0 µm to 500 µm, 1.0 µm to 150 µm, 1.0 µm to 30 µm, 1.0 µm to 10 µm or 1.0 µm to 5.0 µm.

32. The method of any one of embodiments 1-31, wherein one or more of the particles have or comprise particles having a diameter that is substantially the same as the average diameter of a cell in the cell composition or is within 1.5-fold greater or less than the average diameter of a cell in the cell composition.

33. The method of any one of embodiments 1-32, wherein one or more of the particles is magnetic and/or one or more of the particles comprise a magnetic core, a paramagnetic core or a superparamagnetic core.

34. The method of embodiment 33, wherein the magnetic core is selected from among metal oxides, ferrites, metals, hematite, metal alloys, and combinations thereof.

35. The method of any one of embodiments 1-34, wherein one or more of the particles comprise an iron oxide core.

36. The method of any one of embodiments 33-35, wherein the magnetic core comprises a coat.

37. The method of embodiment 36, wherein the coat protects, reduces or prevents the magnetic core from oxidation.

38. The method of embodiment 36 or embodiment 37, wherein the coat comprises a polymer, a polysaccharide, a silica, a fatty acid, a carbon or a combination thereof.

39. The method of any one of embodiments 36-37, wherein the polymer, the polysaccharide, the silica, the fatty acid, the carbon or a combination thereof is biodegradable.

40. The method of embodiment 38 or embodiment 39, wherein the polysaccharide is chitosan, agarose, starch, dextran, a dextran derivative or combinations thereof.

41. The method of embodiment 38 or embodiment 39, wherein the polymer is polyethylene glycol, poly(lactic-co-glycolic acid), polyglutaraldehyde, polyurethane, polystyrene, and polyvinyl alcohol or combinations thereof.

42. The method of any one of embodiments 1-41, wherein the cell has a diameter of between or about between 10 µm and 30 µm.

43. The method of any one of embodiments 1-42, wherein the cell is an animal cell or the cell composition comprises animal cells.

44. The method of any one of embodiments 1-43, wherein the cell is a human cell or the cell composition comprises human cells.

45. The method of any one of embodiments 1-44, wherein the cell is a stem cell or the cell composition comprises stem cells.

46. The method of embodiment 45, wherein the stem cell is an induced pluripotent stem cell (iPSC).

47. The method of any one of embodiments 1-46, wherein the cell is an immune cell or the cell composition comprises immune cells.

48. The method of embodiment 47, wherein the immune cell is a T cell, B cell, macrophage, neutrophil, natural killer (NK) cell or dendritic cell.

49. The method of any one of embodiments 1-48, wherein the cell composition has been mixed with one or more of the particles, wherein the particle comprises a stimulating agent to effect stimulation and/or activation of a cell in the cell composition prior to the one or more incubations in step a).

50. The method of embodiment 49, wherein the cell is a T cell and the stimulating agent is an anti-CD3 antibody and/or anti-CD28 antibody or an antigen-binding fragment thereof.

51. The method of embodiment 50, wherein the cell is an antigen presenting cell and the stimulating agent is an anti-CD80 antibody and/or anti-CD86 antibody or an antigen-binding fragment thereof.

52. The method of any one of embodiments 1-51, wherein the cell composition has been mixed with one or more of the particles, wherein the particle comprises an affinity reagent to effect isolation or enrichment of a cell in the cell composition prior to the one or more incubations in step a).

53. The method of embodiment 52, wherein the affinity reagent comprises an antibody or antigen-binding fragment thereof that specifically binds to a cell surface protein on one or more cells in the cell composition.

54. The method of embodiment 53, wherein the cell surface protein is selected from among CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3.

55. The method of any one of embodiments 1-54, wherein:
the one or more incubation is for at least or at least about 30 seconds, 1 minute, 2 minutes, 3 minutes, 4 minutes, 5 minutes, 10 minutes, 20 minutes or 30 minutes; or
the one or more incubation is from or from about 30 seconds to 30 minutes, 1 minute to 20 minutes, 1 minute to 10 minutes or 1 minute to 5 minutes.

56. The method of any one of embodiments 2-55, wherein:
the volume of the hypotonic and/or hypertonic solution is at least or at least about 1 mL, 3 mL, 9 mL, 12 mL, 15 mL, 18 mL, 20 mL, 25 mL, 30 mL, 35 mL, 40 mL, 45 mL, 50 mL or more; or
the volume of the hypotonic and/or hypertonic solution is from or from about 1 mL to 50 mL, 2 mL to 30 mL, 5 mL to 25 mL or 10 mL to 20 mL.

57. The method of any one of embodiments 1-56, wherein the method does not destroy the surface of the particle or the coat on the surface of the particle or does remove the biomolecule attached to the surface of the particle.

58. The method of any one of embodiments 1-57, wherein the determining in step b) comprises manual counting, electronic particle counting, affinity-based detection, microscopy, flow cytometry, or magnetic cell sorting.

59. The method of any one of embodiments 1-58, wherein the determining in step b) comprises detecting one or more materials or biomolecules present, associated with or attached to the surface of the particles, optionally using a binding agent that specifically binds to the material or biomolecule.

60. The method of embodiment 59, wherein the particles comprising a coat and the coat comprises the material.

61. The method of embodiment 59 or embodiment 60, wherein the material is a polysaccharide.

62. The method of embodiment 61, wherein the material is dextran and/or the binding agent is an anti-dextran antibody.

63. The method of embodiment 59, wherein the biomolecule is an antibody or antigen-binding fragment against a cell surface protein attached to the surface of the particle, which optionally is an anti-CD3 or anti-CD28 antibody.

64. A method of enumerating or detecting the presence or absence of particles in a cell composition, the method comprising the steps of:
a) performing one or more incubations, thereby producing an output composition, wherein the one or more incubations comprise incubating a sample comprising at least a portion of a cell composition or a sample derived from the cell composition, under a condition sufficient to induce lysis of one or more cells in the sample; and
b) determining the presence, absence, number and/or concentration of particles in the output composition using a binding agent that specifically binds to a material, moiety or biomolecule present on, associated with or attached to the particle, thereby enumerating or detecting the presence or absence of particles in the cell composition.

65. The method of embodiment 64, wherein the binding agent is an antibody or antigen-binding fragment thereof.

66. The method of embodiment 64 or embodiment 65, wherein the particle comprises a coat comprising the material.

67. The method of any of embodiments 64-66, wherein the material is a polysaccharide.

68. The method of any of embodiments 64-67, wherein the material is dextran and/or the binding agent is an anti-dextran antibody.

69. The method of embodiment 64 or embodiment 65, wherein the biomolecule is an antibody or antigen-binding fragment against a cell surface protein attached to the surface of the particle, which optionally is an anti-CD3 or anti-CD28 antibody.

70. The method of embodiment 69, wherein the binding agent is an anti-idiotypic or anti-isotypic antibody against the biomolecule.

71. The method of any of embodiments 64-70, wherein the one or more incubations induces osmotic cell lysis of one or more cells in the sample.

72. The method of any of embodiments 62-71, wherein the one or more incubations comprises incubating the sample with a hypotonic solution.

73. The method of embodiment 72, wherein the one or more incubations further comprises incubating the sample with a hypertonic solution.

74. The method of any of embodiments 64-73, wherein the determining comprises fluorescence-activated cell sorting (FACS) for detection of one or more of the particles comprising the coat.

75. The method of any one of embodiments 1-74, wherein the one or more incubations in step a) is/are performed at a temperature that is about 15° C. to 30° C., 18° C. to 28° C. or 20° C. to 25° C.

76. The method of any one of embodiments 1-75, wherein the one or more incubations in step a) is/are performed at a temperature that is about 23° C.

77. An article of manufacture, comprising:
a container comprising a solution for effecting osmotic cell lysis;
packaging material; and
a label or package insert comprising instructions for enumerating or detecting the presence or absence of particles in a cell composition.

78. The article of manufacture of embodiment 77, wherein the solution for effecting osmotic cell lysis is a hypotonic solution.

79. The article of manufacture of embodiment 77 or embodiment 78, further comprising a container comprising a hypertonic solution.

80. The article of manufacture of any of embodiments 77-79, further comprising an instrument or reagent for detecting or identifying particles.

81. The article of manufacture of embodiment 80, wherein the instrument or reagent comprises a hemocytometer.

82. The article of manufacture of embodiment 80, wherein the instrument or reagent comprises an binding agent specific for a material, moiety or biomolecule on the surface of the particle.

83. The article of manufacture of embodiment 82, wherein the binding agent is an antibody or an antigen-binding fragment thereof.

84. The article of manufacture of embodiment 82 or embodiment 83, wherein the particle comprises a coat comprising the material.

85. The article of manufacture of embodiment 84, wherein the material is a polysaccharide.

86. The article of manufacture of any of embodiments 82-85, wherein the material is dextran and/or the binding agent is an anti-dextran antibody.

87. The article of manufacture or embodiment 82 or embodiment 83, wherein the biomolecule is an antibody or antigen-binding fragment against a cell surface protein attached to the surface of the particle, which optionally is an anti-CD3 or anti-CD28 antibody.

88. The article of manufacture of embodiment 87, wherein the binding agent is an anti-idiotypic or anti-isotypic antibody against the biomolecule.

89. The article of manufacture of any of embodiments 82-88, wherein the binding agent is fluorescently labeled.

VII. EXAMPLES

The following examples are included for illustrative purposes only and are not intended to limit the scope of the invention.

Example 1

Cell Lysis with Bleach and Residual Bead Enumeration

In this example, flow cytometry was used to detect the presence of bead particles from among T cells in a composition. Primary human T cells were isolated by affinity-based selection from human PBMC samples obtained from healthy donors. The T cells were mixed with bead particles (e.g., MACSiBead™; Miltenyi Biotec) coupled with an antibody reagent, for example anti-CD28 antibody (isotype mouse IgG1), anti-CD3 antibody (isotype mouse IgG2a), and anti-biotin antibody (e.g. MACS® GMP ExpAct beads) at varying ratios. Exemplary bead particles are silica chromatography microbeads having a diameter of about 3.5 μm and contain a paramagnetic inner core of colloidal iron and dextran microbeads, wherein the inner core is coated with layers of silica, polyurethane and amino-dextran. The coat is linked to anti-CD28 and anti-biotin antibodies and the particles are further loaded with biotinylated anti-CD3 antibodies via an interaction between biotin and the anti-biotin antibody.

Figure 1A:
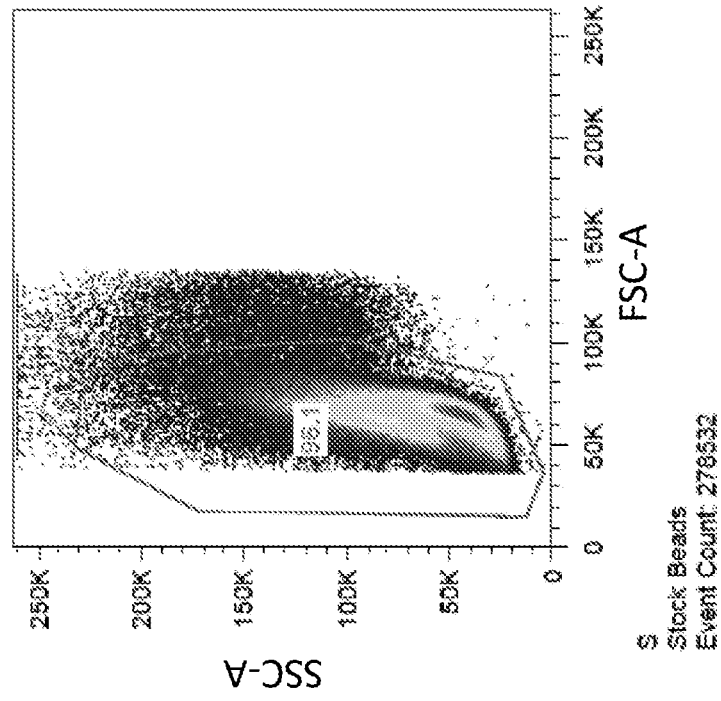
Figure 1C:
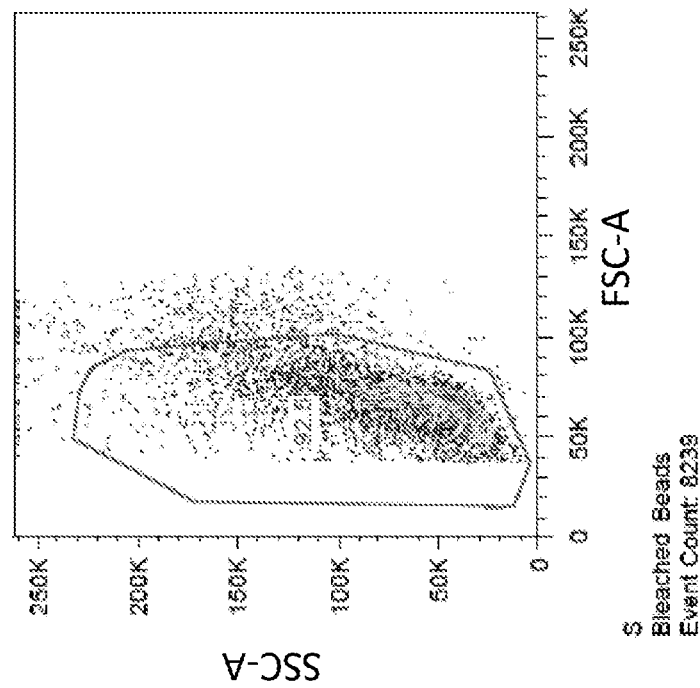
Figure 1D:
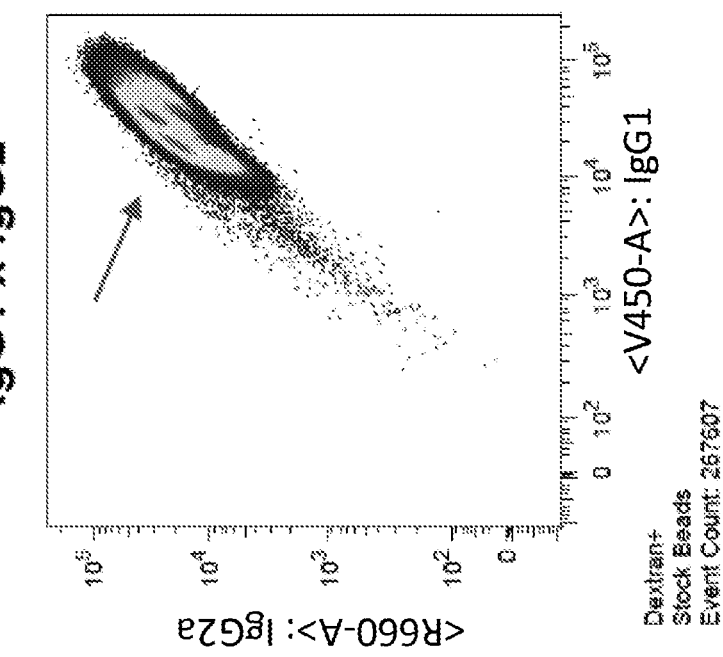
Figure 1E:
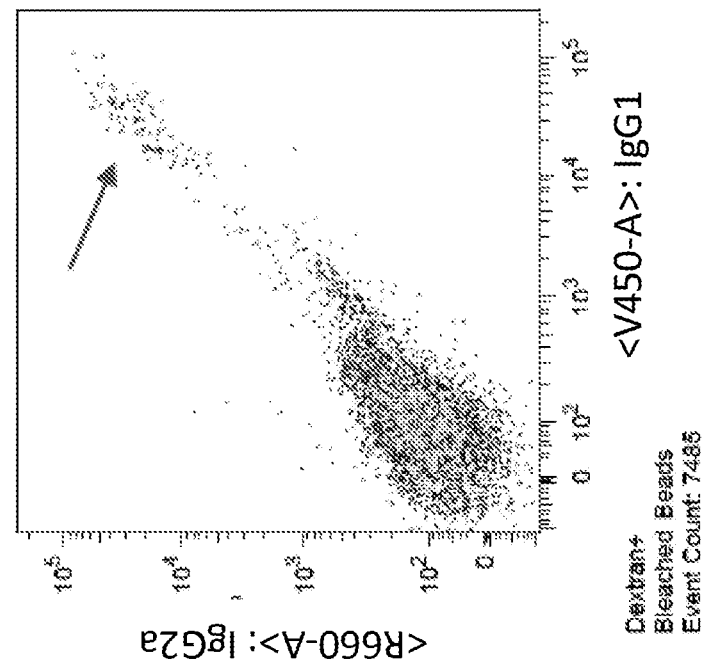
Figure 1F:
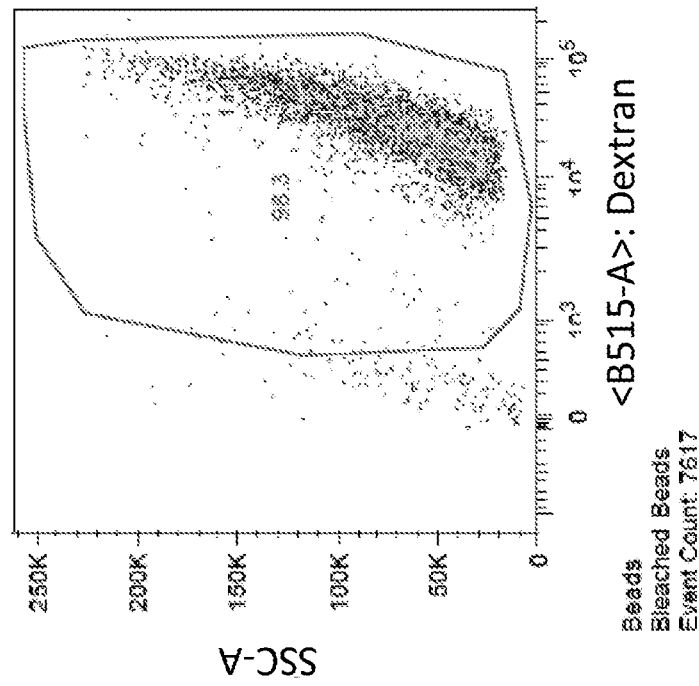

The composition containing cells mixed with bead particles was either treated with bleach or was left untreated. To detect the particles in the composition, samples were stained with a fluorescently labeled anti-mouse IgG1 antibody, fluorescently labeled anti-mouse IgG2a antibody and fluorescently labeled anti-dextran antibody for assessment by flow cytometry. The results showed detection of particles (FIG. 1A) that were positive for dextran (FIG. 1B), IgG1 (FIG. 1C), and IgG2a (FIG. 1C) in the composition that was not treated with bleach. However, in the composition treated with bleach, a significant decrease in the number of event counts of particles was observed (FIG. 1D). The amount of events positive for dextran observed in the bleached sample (FIG. 1E) was significantly reduced as compared to the unbleached sample (FIG. 1B) and the IgG1 and IgG2a staining (FIG. 1F) was almost undetectable. These results showed that the bleach damaged the particles and/or denatured the anti-CD3 antibodies (IgG2a isotype) and anti-CD28 antibodies (IgG1 isotype) on the surface of the particles.

Example 2

Cell Lysis Method for Residual Bead Enumeration in a Cell Sample

In further exemplary methods, a cell lysis method was employed to remove cells from such a solution without damaging the bead particles, thereby allowing accurate bead enumeration. The method involved using hypotonic and hypertonic solutions to osmotically induce lysis of a cell composition that had been incubated in the presence of bead particles, removing residual cellular debris from the mixed bead and cell solution and counting the bead particles present in the sample.

A cell composition containing cells that had been incubated or mixed with bead particles was prepared (in some cases, called a mixed-bead cell composition). In an exemplary embodiment, the mixed-bead cell composition was prepared by incubating or mixing cells, such as T cells, with bead particles coupled with an antibody reagent (e.g., MACS® GMP ExpAct beads; Miltenyi Biotec), for example anti-CD28 antibody and anti-CD3 antibody. In exemplary methods, bead particles contain a paramagnetic inner core of colloidal iron and dextran microbeads, wherein the inner core is coated with layers of silica, polyurethane and amino-dextran. Following incubation, the bead particles were removed from cells in the population using a magnetic removal procedure. From this resulting mixed-bead cell composition, which may contain residual bead particles bound to the surface of the cells, a sample was retained for bead enumeration (in some cases, called "test cell composition," which can be a "residual bead cell composition"). In some cases, optionally, the retained test cell composition was cryopreserved in a cryopreservation solution containing dimethyl sulfoxide (DMSO) prior to enumeration of bead particles.

A 1 mL sample of the test cell composition was retained and assessed for the presence or amount of bead particles in the sample. In embodiments in which the retained test cell composition was cryopreserved, the sample was washed to remove the cryopreservation solution containing DMSO prior to cell lysis. In embodiments in which the retained test cell composition is not cryopreserved, the sample is washed prior to cell lysis. For washing, a sample tube was prepared by adding a 45 mL blocking solution containing 0.2% Human Serum Albumin in Dulbecco's Phosphate-Buffered Saline to a 50 mL tube, and incubating the tube at 37° C. for 32 minutes on a rotator at a speed of 10 rotations per minute. 1 mL of the retained test cell composition was added to the tube containing the blocking solution and the resulting solution was mixed by inverting five times. The solution was subsequently centrifuged at 500×g for 5 minutes and the supernatant was aspirated until only 1 mL of sample remained. The sample was vortexed three times for approximately 5 seconds, each time at a speed of 3000 rpm, with about 2 seconds rest time between each vortex step.

For cell lysis in a hypotonic solution, about 18 mLs of Water for Injection was added to a 1 mL volume of washed or cryopreservative-free test cell composition. To mix the cells and hypotonic solution, the sample was vortexed about five times for approximately 10 seconds, each time at a speed of 3000 rpm, with about 2 seconds rest time between each vortex step. The mixed hypotonic cell sample was incubated at room temperature for about 5 minutes to induce cell lysis.

After the hypotonic incubation, approximately 12 mL of 5M NaCl was added to the hypotonic cell sample to result in a hypertonic solution. The hypertonic cell sample was mixed by vortexing five times for approximately 10 seconds, each time at a speed of about 3000 rpm, with about 2 seconds rest time between each vortex step, and then was incubated at room temperature for about 5 minutes. After incubation, the sample was centrifuged at about 500×g for 5 minutes and the supernatant was aspirated so that a volume between about 1 mL and 2 mL of sample remained. The sample was centrifuged again at about 500×g for 1 minute and the supernatant was removed until only about 1 mL of sample remained (also referred to as "final sample volume" herein). The hypertonic incubation and rinse was used to remove and wash out cellular debris generated during the hypotonic lysis.

For residual bead enumeration, the prepared sample was vortexed for about 20 seconds at a speed of about 3000 rpm. From the liquid collected at the bottom of the tube after vortexing, approximately 115 µL of sample was collected by pipette with a pipette tip that had been prewashed with blocking solution (0.2% Human Albumin Serum in Dulbecco's Phosphate-Buffered Saline). The 115 µL sample was loaded onto a Hausser Nageotte Bright-Line™ Hemocytometer chamber. The loaded hemocytometer was placed in a covered petri dish and allowed to incubate at room temperature for approximately 25 minutes. After incubation, the hemocytometer was viewed with a 20× objective lens and phase contrast condenser annulus on a Nikon Eclipse Ci-L microscope. Bead particles that were visualized in 40 rectangles, including bead particles touching the rectangle lines, of the hemocytometer grid were counted to obtain a "bead particle count." Visualized bead particles were uniformly spherical, had a black outline that was smooth with no jagged edges or corners, and/or had a bright white center. Three replicates of a 115 µL sample were counted in total.

Taking into account that 40 rectangles of a Hausser Nageotte Bright-Line™ Hemocytometer held a total of 50 µL liquid, the number of bead particles in the residual bead cell composition was calculated as follows:

To calculate the number of bead particles per µL of the test cell composition (Beads/µL): Bead count÷50 µL;

To calculate the number of total bead particles in the test cell composition (beads/sample): Beads/µL×Final Retained Sample Volume (e.g., 1 ml).

Assuming the retained test composition had a volume of 1 mL, the beads/sample is the same as the beads/mL of the original mixed bead-cell composition.

In some embodiments, the average, standard deviation and coefficient of variation (100×(standard deviation/average)) of total bead particles per test cell composition can be calculated from at least three replicate samples.

This method resulted in enumeration of undamaged bead particles that were separated from lysed cells, thereby resulting in an improved method for an accurate assessment on the amount of residual bead particles left in a mixed cell and bead composition.

Example 3

Cell Lysis Methods and Residual Bead Enumeration by Hemocytometer

The impact of the number of bead particles in a sample subjected to a cell lysis method on accurate bead enumeration was assessed.

Materials and Methods

Samples

A series of samples was prepared in triplicate containing about $10 \times 10^6$ CAR-expressing T cells that were previously stimulated with a reagent comprising beads linked to anti-CD3 and anti-CD28 antibodies (e.g., MACS® GMP ExpAct beads; Miltenyi Biotec) and debeaded to remove residual bead particles. The debeaded samples were spiked with 250, 500, 1000, or 2000 bead particles linked to anti-CD3 and anti-CD28 antibodies per mL of sample.

Cell Lysis Methods with 50 mL Polypropylene Tube

Each sample was processed using the cell lysis method generally as described in Example 2. Briefly, a sample tube was prepared by adding a blocking solution containing 0.2% Human Serum Albumin in Dulbecco's Phosphate-Buffered Saline to a 50 mL polypropylene tube, and the tube was incubated at 37° C. for 32 minutes on a rotator at a speed of 10 rotations per minute. 1 mL of a prepared sample described above was added to the tube containing the blocking solution and the resulting solution was mixed by inverting five times. The remaining steps were performed as described in Example 2.

Bead Enumeration by Hemocytometer

For bead enumeration, the final sample volume was vortexed for about 20 seconds at a speed of about 3000 rpm. From the liquid collected at the bottom of the tube after vortexing, approximately 115 µL of sample was collected by pipette with a pipette tip that had been prewashed with blocking solution (0.2% Human Albumin Serum in Dulbecco's Phosphate-Buffered Saline). The 115 µL sample was loaded onto a Hausser Nageotte Bright-Line™ Hemocytometer chamber. The loaded hemocytometer was placed in a covered petri dish and allowed to incubate at room temperature for approximately 25 minutes. After incubation, the hemocytometer was viewed with a 20X objective lens and phase contrast condenser annulus on a Nikon Eclipse Ci-L microscope. Bead particles that were visualized in 40 rectangles, including bead particles touching the rectangle lines, of the hemocytometer grid were counted to obtain a "bead particle count." Visualized bead particles were uniformly spherical, had a black outline that was smooth with no jagged edges or corners, and/or had a bright white center. Three replicates of a 115 µL sample were counted in total.

Taking into account that 40 rectangles of a Hausser Nageotte Bright-Line™ Hemocytometer held a total of 50 µL liquid, the number of bead particles in the sample was calculated as follows:

To calculate the number of bead particles per µL of the sample (Beads/µL): Bead count÷50 µL;

To calculate the number of total bead particles in the sample (beads/sample): Beads/µL×Final Retained Sample Volume (e.g., 1 ml).

The average, standard deviation and coefficient of variation (100×(standard deviation/average)) of total bead particles per sample was calculated.

Results

Figure 2:
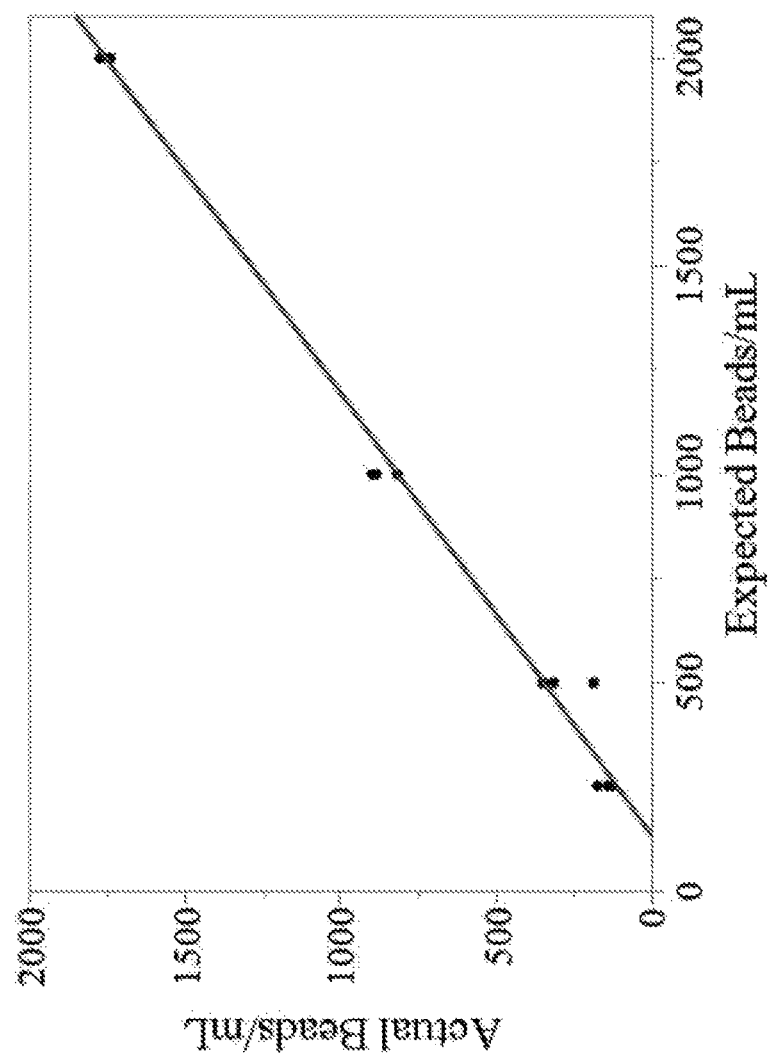
FIG. 2 is a graph showing the number of actual bead particles counted after processing by a method of enumerating bead particles in comparison to the number of bead particles that were expected to be counted after processing. The samples comprise debeaded CAR-expressing T cells mixed with 250, 500, 1000, or 2000 bead particles. Bead particles were enumerated by hemocytometer.

The number of bead particles in the samples, as calculated by hemocytometer as described above, was compared to the corresponding expected number of bead particles in the samples. These data revealed that the bead count was linear between the tested spike amounts of 250 and 2000 beads per mL (FIG. 2).

The method described above was repeated on multiple days (e.g. 2 samples in triplicate with one operator over two days, 1 sample per day or 1 operator assessing 2 samples over three days), and with multiple operators (e.g. 3 operators assessing 2 samples each) to assess inter-operator, inter-day, and intra-assay variability of the method. The intra-assay, inter-operator, and inter-day variability was determined to be within acceptable limits when the bead quantity fell within the linear range of 250 beads/mL to 2000 beads/mL.

Example 4

Cell Lysis Methods and Accuracy of Residual Bead Enumeration

The impact of the number of bead particles in a sample subjected to a cell lysis method on accurate bead enumeration was assessed.

Materials and Methods

Samples

A series of bead only samples (referred to as "bead only" sample) which comprised of 500, 750, 1000, or 1500 of the previously described bead particles linked to anti-CD3 and anti-CD28 antibodies (e.g., MACS® GMP ExpAct beads; Miltenyi Biotec) were prepared in duplicate. A second series of samples was prepared in triplicate which consisted of about $10 \times 10^6$ CAR-expressing T cells that were previously stimulated with a reagent comprising beads linked to anti-CD3 and anti-CD28 antibodies and debeaded to remove residual bead particles. The debeaded samples were spiked with 0, 500, 750, 1000, or 1500 bead particles linked to anti-CD3 and anti-CD28 antibodies. The samples were diluted in a 0.2% human serum albumin solution or 2M NaCl during preparation of the series.

Cell Lysis Methods with 50 mL Polypropylene Tube

Each sample was processed using the cell lysis method as described in Example 2. Briefly, a sample tube was prepared by adding a 45 mL blocking solution containing 0.2% Human Serum Albumin in Dulbecco's Phosphate-Buffered Saline to a 50 mL polypropylene tube, and the tube was incubated at 37° C. for 32 minutes on a rotator at a speed of 10 rotations per minute. 1 mL of a prepared sample described above was added to the tube containing the blocking solution and the resulting solution was mixed by inverting five times. The remaining steps are as described in Example 2.

Bead Enumeration by Hemocytometer

Bead enumeration by both hemocytometer was performed as described in Example 3 above.

Bead Enumeration by Flow Cytometry

For bead enumeration by flow cytometry, about 140 µL of the sample was added to a TruCount™ tube (BD Biosciences) which contained a known number of fluorescent TruCount™ beads. About 20 µL of blocking solution containing 12.5% normal mouse serum was added to the TruCount™ tube and the solution was incubated for five minutes at room temperature. After incubation with the blocking solution, about 40 µL of FITC labeled anti-dextran antibody was added to the tube to achieve a final dilution of 1:40. The tube was then incubated for 25 minutes at room temperature. After incubation with the anti-dextran antibody, about 360 µL of a blocking solution (0.2% Human Serum Albumin in Dulbecco's Phosphate-Buffered Saline) was added to each tube to reach a final sample volume of about 560 µL. The samples were then acquired on a flow cytometer until a target of about 25 to 30,000 TruCount events was counted. The absolute number of dextran stained beads (beads/µL) in the sample was determined by comparing the number of dextran events to TruCount bead events.

Results

The percentages of counted bead particles relative to the actual number of bead particles spiked in the sample were calculated in the series containing bead particles only and in the series containing cells mixed with bead particles.

Figure 3:
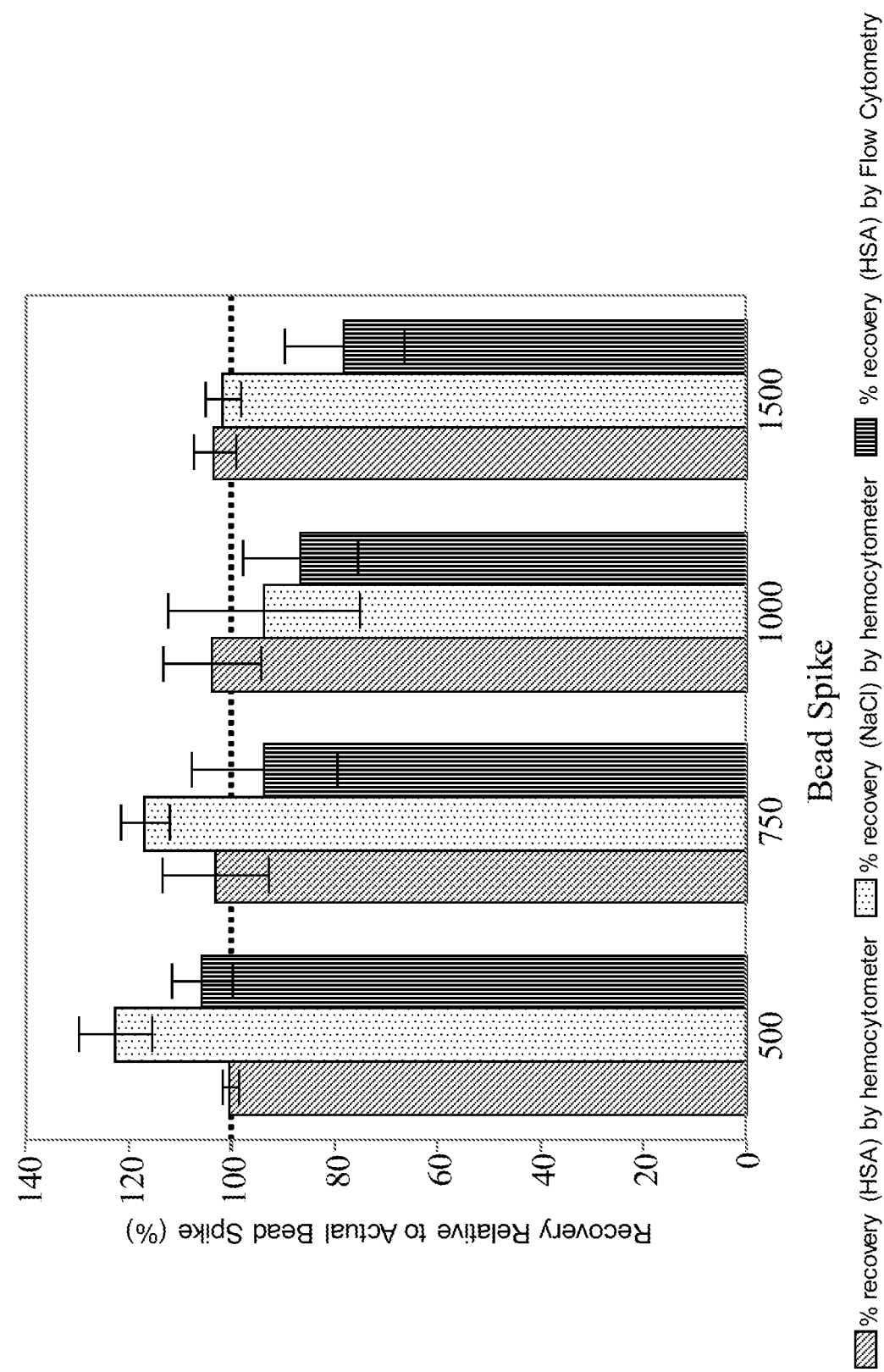
FIG. 3 is a graph showing the percentage of bead particles counted relative to the actual number of beads spiked in samples containing increasing loads of bead particles alone in solution containing human serum albumin (HSA) and subjected to a cell lysis method (NaCl). Bead particles were enumerated by hemocytometer or flow cytometry.

In the bead particles only series, enumeration of bead particles was comparable between the hemocytometer and flow cytometry bead detection methods (FIG. 3). The accuracy of bead enumeration in samples diluted in 0.2% human serum albumin (HSA) versus 2M NaCl was consistent as assessed by hemocytometer (FIG. 3). Overall, the enumeration of bead particles from the bead only samples was comparable across the series whether detected by hemocytometer or flow cytometry and irrespective of the sample diluent (FIG. 3).

Figure 4:
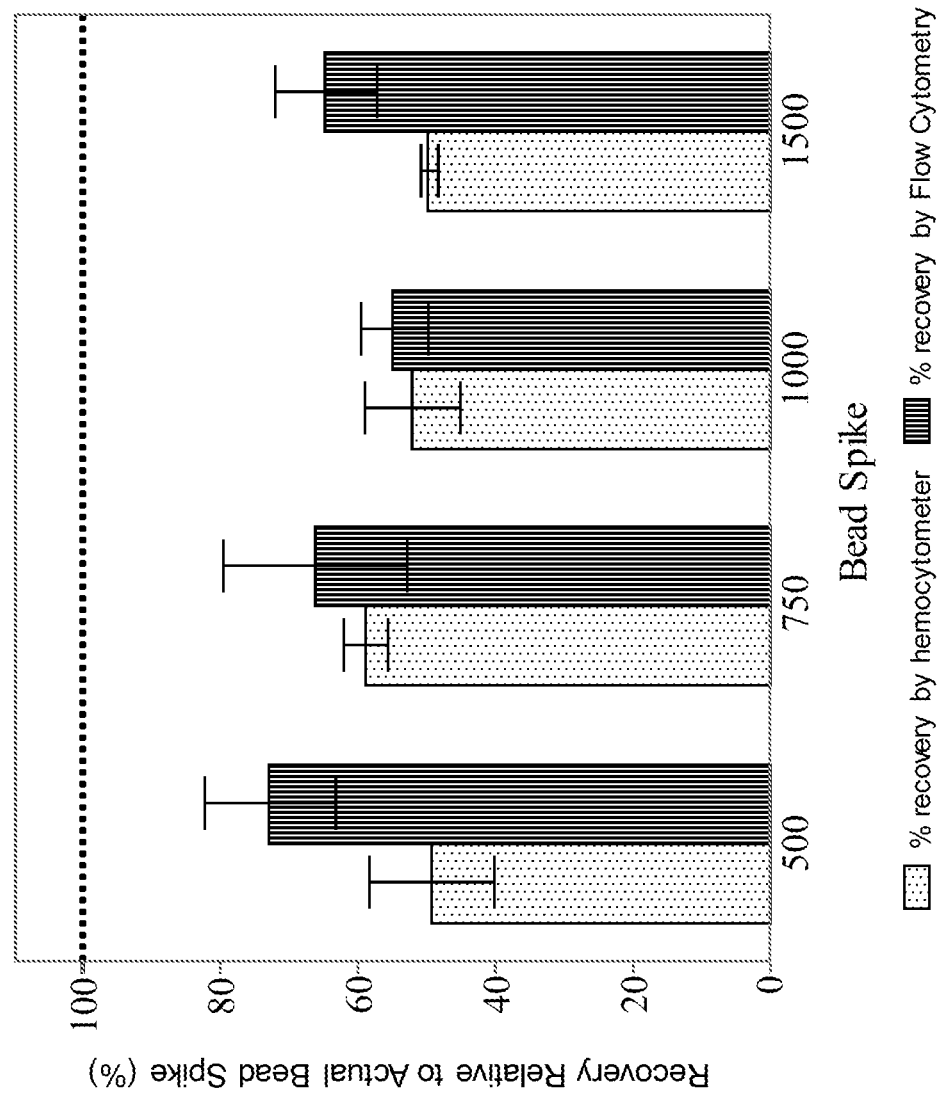
FIG. 4 is a graph showing the percentage of bead particles counted relative to the actual number of beads spiked in samples containing increasing loads of bead particles mixed with cells and subjected to a cell lysis method. Bead particles were enumerated by hemocytometer or flow cytometry.

In the bead particles mixed with cells series, enumeration of bead particles was comparable between the hemocytometer and flow cytometry bead detection methods (FIG. 4). Overall, the enumeration of bead particles from the bead mixed with cells samples was comparable across the series whether detected by hemocytometer or flow cytometry and irrespective of the number of bead particles in the sample (FIG. 4).

Altogether, these results indicate that the number or load of bead particles in a sample with or without cells does not impact the ability to consistently enumerate bead particles by either hemocytometer or flow cytometry.

Example 5

Bead Types, Cell Lysis Methods and Residual Bead Enumeration

The number of residual bead particles in cell samples subjected to three different debeading processes was determined.

Materials and Methods

Samples

Two control samples were prepared in triplicate: 1) control sample with $4 \times 10^6$ CAR-expressing T cells that were previously stimulated with a reagent comprising bead particles linked to anti-CD3 and anti-CD28 antibodies; and 2) control sample with $4 \times 10^6$ CAR-expressing T cells that were previously stimulated with a reagent comprising bead particles linked to anti-CD3 and anti-CD28 antibodies mixed with 500 of the previously described bead particles. Three test samples containing $3.8 \times 10^6$ CAR-expressing T cells that were previously stimulated with a reagent comprising bead particles linked to anti-CD3 and anti-CD28 antibodies were prepared in triplicate: 1) test sample that was debeaded with the CliniMACS® System (Miltenyi Biotec); 2) test sample that was debeaded with the DynaMag™ CTS™ Magnet (Gibco); and 3) test sample that was debeaded with a modified protocol using a the DynaMag™ CTS™ Magnet (Gibco) in which the draining flow-rate off the magnet was controlled to between 10 mL to 20 mL per minute by placing tubing between the source bag on the magnet and the capture bag on the magnet shelf (referred to herein as the "modified DynaMag debeading process").

Cell Lysis Methods with 50 mL Polypropylene Tube

Each sample was processed using the cell lysis method as described in Example 2. Briefly, a sample tube was prepared by adding a 45 mL blocking solution containing 0.2% Human Serum Albumin in Dulbecco's Phosphate-Buffered Saline to a 50 mL polypropylene tube, and the tube was incubated at 37° C. for 32 minutes on a rotator at a speed of 10 rotations per minute. 1 mL of a prepared sample described above was added to the tube containing the blocking solution and the resulting solution was mixed by inverting five times. The remaining steps are as described in Example 2.

Bead Enumeration by Hemocytometer

Bead enumeration was performed as outlined in Example 3 above.

Results

The number of bead particles per ml in the in the control samples was calculated and it was determined that the bead loss in the control was about 25%. The number of bead particles in the debeaded test samples was normalized against the 25% bead loss in the control sample. Debeading using the DynaMag™ CTS™ Magnet left 3-fold more residual bead particles as compared to the modified DynaMag debeading process (Table 1). Debeading using the CliniMACS® System resulted in fewer residual bead particles as compared to debeading with the other two methods (Table 1).

TABLE 1

Residual Bead Enumeration

| | Total Bead/mL Normalized for 25% Bead Loss | | | Total Beads/mL + 100% | | |
|---|---|---|---|---|---|---|
| Sample | Mean | Standard Deviation | Coefficient of Variation | Mean | Standard Deviation | Coefficient of Variation |
| CliniMacs ® | 11.67 | 8.08 | 69.28 | 23.33 | 16.17 | 69.28 |
| DynaMag ™ | 797.67 | 42.19 | 5.29 | 1595 | 83.86 | 5.26 |
| Modified DynaMag ™ | 273.67 | 72.46 | 26.48 | 547 | 144.60 | 26.43 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for enumerating or detecting the presence or absence of residual bead particles in a cell composition, the method comprising the steps of:
   a) incubating a sample comprising at least a portion of the cell composition that is suspected of comprising residual bead particles with a hypotonic solution under a condition sufficient to induce osmotic lysis of one or more cells in the sample to produce a lysed cell composition, and
   incubating at least a portion of the lysed cell composition with a hypertonic solution; and
   b) determining the presence, absence, number and/or concentration of residual bead particles in the output composition, thereby enumerating or detecting the presence or absence of residual bead particles in the cell composition.

2. The method of claim 1, wherein the cell composition is produced by a method comprising:
   (1) mixing a population of cells with one or more bead particles thereby generating an input composition; and
   (2) removing one or more of the bead particles from the cells in the input composition, thereby producing the cell composition.

3. The method of claim 2, wherein the surface of one or more of the bead particles comprise a material or a biomolecule capable of binding to a macromolecule on the surface of one or more cells in the composition.

4. The method of claim 1, wherein step a) further comprises rinsing or washing the output composition.

5. The method of claim 1, wherein:
   the hypotonic solution has an osmolarity between at or about 0 mOsm/L and at or about 270 mOsm/L;
   the hypotonic solution comprises a solute concentration of between at or about 0 mM and at or about 140 mM; and/or
   the hypotonic solution comprises a percentage weight per volume (% w/v) of solute of between at or about 0% and at or about 0.8%.

6. The method of claim 1, wherein the hypotonic solution is sterile water for injection.

7. The method of claim 1, wherein:
   the hypertonic solution has an osmolarity of between at or about 300 mOsm/L and at or about 5000 mOsm/L;
   the hypertonic solution has a solute concentration of between at or about 200 mM and at or about 5000 mM; and/or
   the hypertonic solution comprises a percentage weight per volume (% w/v) of solute of between at or about 1.5% and at or about 15%.

8. The method of claim 1, wherein the hypertonic solution comprises a solute that is NaCl.

9. The method of claim 1, wherein
   the concentration of the cell composition is at least or at least about $2 \times 10^5$ cells/mL.

10. The method of claim 9, wherein:
    the volume of the cell composition is from at or from about 0.2 mL to at or about 50 mL.

11. The method of claim 1, wherein one or more of the residual bead particles are residual bead particles having a diameter of at or about 1.0 μm to at or about 500 μm.

12. The method of claim 1, wherein one or more of the residual bead particles are residual bead particles having a diameter that is substantially the same as the average diameter of a cell in the cell composition or is within 1.5-fold greater or less than the average diameter of a cell in the cell composition.

13. The method of claim 1, wherein one or more of the residual bead particles are magnetic and/or one or more of the residual bead particles comprise a magnetic core, a paramagnetic core or a superparamagnetic core.

14. The method of claim 1, wherein the cell is an immune cell or the cell composition comprises immune cells or the cell is a stem cell or the cell composition comprises stem cells.

15. The method of claim 1, wherein:
    one or both incubations are from at or about 30 seconds to at or about 30 minutes.

16. The method of claim 1, wherein:
the volume of the hypotonic and/or hypertonic solution is from at or about 1 mL to at or about 50 mL.

17. The method of claim 1, wherein: the determining in step b) comprises manual counting, electronic particle counting, affinity-based detection, microscopy, flow cytometry, or magnetic cell sorting.

18. The method of claim 1, wherein the determining in step b) comprises detecting one or more materials or biomolecules present on, associated with or attached to the surface of the residual bead particles, using a binding agent that specifically binds to the material or the biomolecule.

19. The method of claim 18, wherein the material is dextran and/or the binding agent is an anti-dextran antibody.

20. The method of claim 18, wherein the biomolecule is an antibody or antigen-binding fragment against a cell surface macromolecule attached to the surface of the residual bead particle.

21. The method of claim 1, wherein one or both incubations in step a) are performed at a temperature that is at or about 20° C. to at or about 25° C.

22. A method of enumerating or detecting the presence or absence of residual bead particles in a cell composition, the method comprising the steps of:
a) incubating a sample comprising at least a portion of the cell composition that is suspected of comprising residual bead particles with a hypotonic solution under a condition sufficient to induce lysis of one or more cells in the sample to produce a lysed cell composition, and
incubating at least a portion of the lysed cell composition with a hypertonic solution; and
b) determining the presence, absence, number and/or concentration of residual bead particles in the output composition using a binding agent that specifically binds to a material or a biomolecule present on, associated with or attached to the residual bead particle, thereby enumerating or detecting the presence or absence of residual bead particles in the cell composition.

23. The method of claim 22, wherein the material is dextran and/or the binding agent is an anti-dextran antibody.

24. The method of claim 22, wherein the biomolecule is an antibody or antigen-binding fragment against a cell surface macromolecule attached to the surface of the residual bead particle.

25. The method of claim 22, wherein the one or more incubations induces osmotic cell lysis of one or more cells in the sample.

26. The method of claim 22, wherein the determining comprises flow cytometry or fluorescence-activated cell sorting (FACS) for detection of one or more of the residual bead particles or the material or the biomolecule present on, associated with or attached to the residual bead particle.

* * * * *